United States Patent
Chatterton et al.

(10) Patent No.: US 9,476,047 B2
(45) Date of Patent: Oct. 25, 2016

(54) RNAI-MEDIATED INHIBITION OF CONNEXIN 43 FOR TREATMENT OF IOP-RELATED CONDITIONS

(71) Applicant: Arrowhead Research Corporation, Pasadena, CA (US)

(72) Inventors: Jon E. Chatterton, Aliso Viejo, CA (US); Abbot F. Clark, Arlington, TX (US); Martin B. Wax, Westlake, TX (US)

(73) Assignee: Arrowhead Pharmaceuticals, Inc., Pasadena, CA (US)

( * ) Notice: Subject to any disclaimer, the term of this patent is extended or adjusted under 35 U.S.C. 154(b) by 0 days.

(21) Appl. No.: 14/859,484

(22) Filed: Sep. 21, 2015

(65) Prior Publication Data
US 2016/0002638 A1    Jan. 7, 2016

(51) Int. Cl.
C12N 15/11    (2006.01)
A61K 48/00    (2006.01)
C12N 15/113   (2010.01)
A61K 31/713   (2006.01)

(52) U.S. Cl.
CPC .......... *C12N 15/113* (2013.01); *A61K 31/713* (2013.01); *C12N 15/1138* (2013.01); *C12N 2310/11* (2013.01); *C12N 2310/14* (2013.01); *C12N 2320/30* (2013.01)

(58) Field of Classification Search
USPC ........................... 536/23.1, 24.3, 24.33, 24.5
See application file for complete search history.

(56) References Cited

U.S. PATENT DOCUMENTS

| | | | |
|---|---|---|---|
| 7,521,191 B2* | 4/2009 | Khvorova | C12N 15/111 435/6.11 |
| 2005/0119211 A1 | 6/2005 | Chowrira et al. | |
| 2007/0185318 A1 | 8/2007 | Khvorova et al. | |
| 2007/0244062 A1 | 10/2007 | Laux et al. | |

OTHER PUBLICATIONS

Altschul et al.; "Basic Local Alignment Search Tool"; J. Mol. Biol.; vol. 215; pp. 403-410; (1990).
Brummelkamp et al.; "A system for stable expression of short interfering RNAs in mammalian cells"; Science; vol. 296; pp. 550-553; (2002).
Calera et al.; "Connexin43 is required for production of the aqueous humor in the murine eye"; Journal of Cell Science; vol. 199; pp. 4510-4519; (2006).
Berkhout, B.; J. Formos Med Assoc.; 107(10); 749-750; (2008).
Campochiaro, "Potential applications for RNAi to probe pathogenesis and develop new treatments for ocular disorders"; Gene Therapy; vol. 13; pp. 559-562; (2006).
Castanotto, D. et al.; "Functional siRNA expression from transfected PCR products"; RNA; vol. 8; pp. 1454-1460; (2002).
Coffey et al.; "Molecular profiling and cellular localization of connexin isoforms in the rat ciliary epithelium."; Experimental Eye Research; vol. 75; No. 1; pp. 9-21; (2002).
Kim et al.; "Inhibition of ocular angiogenesis by siRNA targeting vascular endothelial growth factor pathway genes"; American Journal of Pathology; vol. 165; No. 6; pp. 2177-2185; (2004).

(Continued)

*Primary Examiner* — Terra C Gibbs

(57) ABSTRACT

RNA interference is provided for inhibition of connexin 43 (Cx43) in intraocular pressure-related conditions, including ocular hypertension and glaucoma such as normal tension glaucoma and open angle glaucoma.

13 Claims, 1 Drawing Sheet

(56) References Cited

OTHER PUBLICATIONS

Kim et al.; "Synthetic dsRNA dicer substrates enhance RNAi potency and efficacy"; Nature Biotechnology; vol. 23; No. 2; pp. 222-226; (2005).
Kleinman et al.; "Sequence-and target-independent angiogenesis suppression by siRNA via TLR3"; Nature; 452 (7187); 591-597; (2008).
Saxena et al.; "Small RNAs with imperfect match to endogenous mRNA repress translation"; The Journal of Biological Chemistry; vol. 278; No. 45; pp. 44312-44319; (2003).
"siRNA Design Guidelines," Ambion Inc.
Stelling et al.; "Functional coupling in bovine ciliary epithelial cells is modulated by carbachol." American Journal of Physiology—Cell Physiology vol. 273(6 Pt 1):C1876-C1881; (1997).
Tuschl, T. et al., "The siRNA User Guide," revised May 6, 2004.
Wolosin et al.; "Effect of heptanol on the short circuit currents of cornea and ciliary body demonstrates rate limiting role of heteroceullular gap junctions in active ciliary body transport."; Exp. Eye Res.; vol. 64; pp. 945-952 (1997).
GenBank Accession No. NM_000165.
GenBank Accession No. NM_000942.
GenBank Accession No. NM_174068.
International Written Opinion for corresponding Application No. PCT/US2009/034023.

* cited by examiner

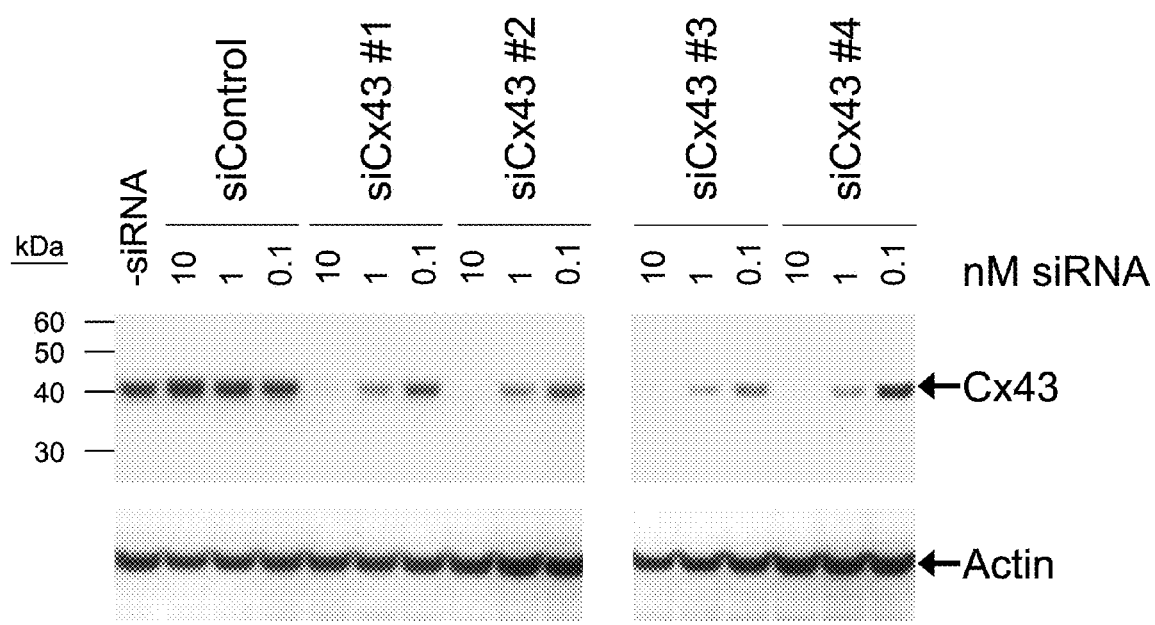

SEQUENCE LISTING

```
<160> NUMBER OF SEQ ID NOS: 81

<210> SEQ ID NO 1
<211> LENGTH: 3130
<212> TYPE: DNA
<213> ORGANISM: Homo Sapiens

<400> SEQUENCE: 1
gagtcagtgg cttgaaactt ttaaaagctc tgtgctccaa gttacaaaaa agcttttacg      60
```

```
aggtatcagc acttttcttt cattaggggg aaggcgtgag gaaagtacca aacagcagcg    120
gagttttaaa ctttaaatag acaggtctga gtgcctgaac ttgccttttc attttacttc    180
atcctccaag gagttcaatc acttggcgtg acttcactac ttttaagcaa aagagtggtg    240
cccaggcaac atgggtgact ggagcgcctt aggcaaactc cttgacaagg ttcaagccta    300
ctcaactgct ggagggaagg tgtggctgtc agtactttc attttccgaa tcctgctgct    360
ggggacagcg gttgagtcag cctggggaga tgagcagtct gcctttcgtt gtaacactca    420
gcaacctggt tgtgaaaatg tctgctatga caagtctttc ccaatctctc atgtgcgctt    480
ctgggtcctg cagatcatat ttgtgtctgt acccacactc ttgtacctgg ctcatgtgtt    540
ctatgtgatg cgaaaggaag agaaactgaa caagaaagag gaagaactca aggttgccca    600
aactgatggt gtcaatgtgg acatgcactt gaagcagatt gagataaaga gttcaagta    660 cggtattgaa gagcatggta aggtgaaaat gcgaggggg ttgctgcgaa cctacatcat    720
cagtatcctc ttcaagtcta tctttgaggt ggccttcttg ctgatccagt ggtacatcta    780
tggattcagc ttgagtgctg tttacacttg caaaagagat ccctgcccac atcaggtgga    840
ctgtttcctc tctcgcccca cggagaaaac catcttcatc atcttcatgc tggtggtgtc    900
cttggtgtcc ctggccttga atatcattga actcttctat gttttcttca agggcgttaa    960
ggatcgggtt aagggaaaga gcgacccta ccatgcgacc agtggtgcgc tgagccctgc    1020
caaagactgt gggtctcaaa aatatgctta tttcaatggc tgctcctcac aaccgctcc    1080 cctctcgcct atgtctcctc ctgggtacaa gctggttact ggcgacagaa acaattcttc    1140
ttgccgcaat tacaacaagc aagcaagtga gcaaaactgg gctaattaca gtgcagaaca    1200
aaatcgaatg gggcaggcgg gaagcaccat ctctaactcc catgcacagc cttttgattt    1260
ccccgatgat aaccagaatt ctaaaaaact agctgctgga catgaattac agccactagc    1320
cattgtggac cagcgacctt caagcagagc cagcagtcgt gccagcagca gacctcggcc    1380
tgatgacctg gagatctaga tacaggcttg aaagcatcaa gattccactc aattgtggag    1440
aagaaaaaag gtgctgtaga aagtgcacca ggtgttaatt ttgatccggt ggaggtggta    1500
ctcaacagcc ttattcatga ggcttagaaa acacaaagac attagaatac ctaggttcac    1560
tgggggtgta tgggggtagat gggtggagag ggaggggata agagaggtgc atgttggtat    1620
ttaaagtagt ggattcaaag aacttagatt ataaataaga gttccattag gtgatacata    1680
gataagggct ttttctcccc gcaaacaccc ctaagaatgg ttctgtgtat gtgaatgagc    1740
gggtggtaat tgtggctaaa tattttgtt ttaccaagaa actgaaataa ttctggccag    1800
gaataaatac ttcctgaaca tcttaggtct tttcaacaag aaaagacag aggattgtcc    1860 ttaagtccct gctaaaacat tccattgtta aaatttgcac tttgaaggta gcttttctag    1920 gcctgacct ccaggtgtca atggacttgt gctactatat tttttattc ttggtatcag    1980 tttaaaattc agacaaggcc cacagaataa gattttccat gcatttgcaa atacgtatat    2040 tcttttttcca tccacttgca caatatcatt accatcactt tttcatcatt cctcagctac    2100
tactcacatt catttaatgg tttctgtaaa cattttaag acagttggga tgtcacttaa    2160
catttttttt ttgagctaaa gtcagggaat caagccatgc ttaatattta acaatcactt    2220
atatgtgtgt cgaagagttt gttttgtttg tcatgtattg gtacaagcag atacagtata    2280
aactcacaaa cacagatttg aaaataatgc acatatggtg ttcaaatttg aacctttctc    2340 atggatttt gtggtgtggg ccaatatggt gtttacatta tataattcct gctgtggcaa    2400
```

```
gtaaagcaca cttttttttt ctcctaaaat gttttccct gtgtatccta ttatggatac    2460
tggttttgtt aattatgatt ctttatttc tctccttttt ttaggatata gcagtaatgc    2520
tattactgaa atgaatttcc tttttctgaa atgtaatcat tgatgcttga atgatagaat    2580
tttagtactg taaacaggct ttagtcatta atgtgagaga cttagaaaaa atgcttagag    2640
tggactatta aatgtgccta aatgaatttt gcagtaactg gtattcttgg gttttcctac    2700
ttaatacaca gtaattcaga acttgtattc tattatgagt ttagcagtct tttggagtga    2760
ccagcaactt tgatgtttgc actaagattt tatttggaat gcaagagagg ttgaaagagg    2820
attcagtagt acacatacaa ctaatttatt tgaactatat gttgaagaca tctaccagtt    2880
tctccaaatg ccttttttaa aactcatcac agaagattgg tgaaaatgct gagtatgaca    2940
cttttcttct tgcatgcatg tcagctacat aaacagtttt gtacaatgaa aattactaat    3000
ttgtttgaca ttccatgtta aactacggtc atgttcagct tcattgcatg taatgtagac    3060
ctagtccatc agatcatgtg ttctggagag tgttctttat tcaataaagt tttaatttag    3120
tataaacata                                                          3130

<210> SEQ ID NO 2
<211> LENGTH: 19
<212> TYPE: DNA
<213> ORGANISM: Artificial
<220> FEATURE:
<223> OTHER INFORMATION: Synthetic oligonucleotide

<400> SEQUENCE: 2
taggcaaact ccttgacaa                                                 19

<210> SEQ ID NO 3
<211> LENGTH: 21
<212> TYPE: RNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (20)..(21)
<223> OTHER INFORMATION: n is any nucleotide a, c, t, g, or u

<400> SEQUENCE: 3
uaggcaaacu ccuugacaan n                                              21

<210> SEQ ID NO 4
<211> LENGTH: 21
<212> TYPE: RNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (20)..(21)
<223> OTHER INFORMATION: n is any nucleotide a, c, t, g, or u

<400> SEQUENCE: 4
uugucaagga guuugccuan n                                              21

<210> SEQ ID NO 5
<211> LENGTH: 21
<212> TYPE: RNA
<213> ORGANISM: Artificial
<220> FEATURE:
<223> OTHER INFORMATION: Synthetic oligonucleotide

<400> SEQUENCE: 5
```

```
uaggcaaacu ccuugacaau u                                              21

<210> SEQ ID NO 6
<211> LENGTH: 21
<212> TYPE: RNA
<213> ORGANISM: Artificial
<220> FEATURE:
<223> OTHER INFORMATION: Synthetic oligonucleotide

<400> SEQUENCE: 6
uugucaagga guuugccuau u                                              21

<210> SEQ ID NO 7
<211> LENGTH: 19
<212> TYPE: RNA
<213> ORGANISM: Artificial
<220> FEATURE:
<223> OTHER INFORMATION: Synthetic oligonucleotide

<400> SEQUENCE: 7
uaggcaaacu ccuugacaa                                                 19

<210> SEQ ID NO 8
<211> LENGTH: 19
<212> TYPE: RNA
<213> ORGANISM: Artificial
<220> FEATURE:
<223> OTHER INFORMATION: Synthetic oligonucleotide

<400> SEQUENCE: 8
uugucaagga guuugccua                                                 19

<210> SEQ ID NO 9
<211> LENGTH: 48
<212> TYPE: RNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (20)..(27)
<223> OTHER INFORMATION: n is any nucleotide a, c, t, g, or u

<400> SEQUENCE: 9
uaggcaaacu ccuugacaan nnnnnnnuug ucaaggaguu ugccuauu                 48

<210> SEQ ID NO 10
<211> LENGTH: 25
<212> TYPE: RNA
<213> ORGANISM: Artificial
<220> FEATURE:
<223> OTHER INFORMATION: Synthetic oligonucleotide

<400> SEQUENCE: 10
uaggcaaacu ccuugacaag guuca                                          25

<210> SEQ ID NO 11
<211> LENGTH: 25
<212> TYPE: RNA
<213> ORGANISM: Artificial
<220> FEATURE:
<223> OTHER INFORMATION: Synthetic oligonucleotide

<400> SEQUENCE: 11
uaggcaaacu ccuugacaag guuca                                          25
```

```
<210> SEQ ID NO 12
<211> LENGTH: 27
<212> TYPE: RNA
<213> ORGANISM: Artificial
<220> FEATURE:
<223> OTHER INFORMATION: Synthetic oligonucleotide

<400> SEQUENCE: 12
ugaaccuugu caaggaguuu gccuauu                                              27

<210> SEQ ID NO 13
<211> LENGTH: 19
<212> TYPE: DNA
<213> ORGANISM: Artificial
<220> FEATURE:
<223> OTHER INFORMATION: Synthetic oligonucleotide

<400> SEQUENCE: 13
ccttaggcaa actccttga                                                       19

<210> SEQ ID NO 14
<211> LENGTH: 19
<212> TYPE: DNA
<213> ORGANISM: Artificial
<220> FEATURE:
<223> OTHER INFORMATION: Synthetic oligonucleotide

<400> SEQUENCE: 14
taggcaaact ccttgacaa                                                       19

<210> SEQ ID NO 15
<211> LENGTH: 19
<212> TYPE: DNA
<213> ORGANISM: Artificial
<220> FEATURE:
<223> OTHER INFORMATION: Synthetic oligonucleotide

<400> SEQUENCE: 15
cagtctgcct ttcgttgta                                                       19

<210> SEQ ID NO 16
<211> LENGTH: 19
<212> TYPE: DNA
<213> ORGANISM: Artificial
<220> FEATURE:
<223> OTHER INFORMATION: Synthetic oligonucleotide

<400> SEQUENCE: 16
tatgacaagt ctttcccaa                                                       19

<210> SEQ ID NO 17
<211> LENGTH: 19
<212> TYPE: DNA
<213> ORGANISM: Artificial
<220> FEATURE:
<223> OTHER INFORMATION: Synthetic oligonucleotide

<400> SEQUENCE: 17
atgacaagtc tttcccaat                                                       19

<210> SEQ ID NO 18
<211> LENGTH: 19
<212> TYPE: DNA
<213> ORGANISM: Artificial
<220> FEATURE:
<223> OTHER INFORMATION: Synthetic oligonucleotide
```

```
<400> SEQUENCE: 18
gtacctggct catgtgttc                                              19

<210> SEQ ID NO 19
<211> LENGTH: 19
<212> TYPE: DNA
<213> ORGANISM: Artificial
<220> FEATURE:
<223> OTHER INFORMATION: Synthetic oligonucleotide

<400> SEQUENCE: 19
aggaagagaa actgaacaa                                              19

<210> SEQ ID NO 20
<211> LENGTH: 19
<212> TYPE: DNA
<213> ORGANISM: Artificial
<220> FEATURE:
<223> OTHER INFORMATION: Synthetic oligonucleotide

<400> SEQUENCE: 20
gaagagaaac tgaacaaga                                              19

<210> SEQ ID NO 21
<211> LENGTH: 19
<212> TYPE: DNA
<213> ORGANISM: Artificial
<220> FEATURE:
<223> OTHER INFORMATION: Synthetic oligonucleotide

<400> SEQUENCE: 21
gagaaactga acaagaaag                                              19

<210> SEQ ID NO 22
<211> LENGTH: 19
<212> TYPE: DNA
<213> ORGANISM: Artificial
<220> FEATURE:
<223> OTHER INFORMATION: Synthetic oligonucleotide

<400> SEQUENCE: 22
agaaactgaa caagaaaga                                              19

<210> SEQ ID NO 23
<211> LENGTH: 19
<212> TYPE: DNA
<213> ORGANISM: Artificial
<220> FEATURE:
<223> OTHER INFORMATION: Synthetic oligonucleotide

<400> SEQUENCE: 23
actcaaggtt gcccaaact                                              19

<210> SEQ ID NO 24
<211> LENGTH: 19
<212> TYPE: DNA
<213> ORGANISM: Artificial
<220> FEATURE:
<223> OTHER INFORMATION: Synthetic oligonucleotide

<400> SEQUENCE: 24
ccaaactgat ggtgtcaat                                              19
```

<210> SEQ ID NO 25
<211> LENGTH: 19
<212> TYPE: DNA
<213> ORGANISM: Artificial
<220> FEATURE:
<223> OTHER INFORMATION: Synthetic oligonucleotide

<400> SEQUENCE: 25
tggacatgca cttgaagca                                            19

<210> SEQ ID NO 26
<211> LENGTH: 19
<212> TYPE: DNA
<213> ORGANISM: Artificial
<220> FEATURE:
<223> OTHER INFORMATION: Synthetic oligonucleotide

<400> SEQUENCE: 26
gacatgcact tgaagcaga                                            19

<210> SEQ ID NO 27
<211> LENGTH: 19
<212> TYPE: DNA
<213> ORGANISM: Artificial
<220> FEATURE:
<223> OTHER INFORMATION: Synthetic oligonucleotide

<400> SEQUENCE: 27
acatgcactt gaagcagat                                            19

<210> SEQ ID NO 28
<211> LENGTH: 19
<212> TYPE: DNA
<213> ORGANISM: Artificial
<220> FEATURE:
<223> OTHER INFORMATION: Synthetic oligonucleotide

<400> SEQUENCE: 28
cacttgaagc agattgaga                                            19

<210> SEQ ID NO 29
<211> LENGTH: 19
<212> TYPE: DNA
<213> ORGANISM: Artificial
<220> FEATURE:
<223> OTHER INFORMATION: Synthetic oligonucleotide

<400> SEQUENCE: 29
acttgaagca gattgagat                                            19

<210> SEQ ID NO 30
<211> LENGTH: 19
<212> TYPE: DNA
<213> ORGANISM: Artificial
<220> FEATURE:
<223> OTHER INFORMATION: Synthetic oligonucleotide

<400> SEQUENCE: 30
cttgaagcag attgagata                                            19

<210> SEQ ID NO 31
<211> LENGTH: 19
<212> TYPE: DNA
<213> ORGANISM: Artificial
<220> FEATURE:

<223> OTHER INFORMATION: Synthetic oligonucleotide

<400> SEQUENCE: 31
tgaagcagat tgagataaa                                                    19

<210> SEQ ID NO 32
<211> LENGTH: 19
<212> TYPE: DNA
<213> ORGANISM: Artificial
<220> FEATURE:
<223> OTHER INFORMATION: Synthetic oligonucleotide

<400> SEQUENCE: 32
aagcagattg agataaaga                                                    19

<210> SEQ ID NO 33
<211> LENGTH: 19
<212> TYPE: DNA
<213> ORGANISM: Artificial
<220> FEATURE:
<223> OTHER INFORMATION: Synthetic oligonucleotide

<400> SEQUENCE: 33
gcagattgag ataaagaag                                                    19

<210> SEQ ID NO 34
<211> LENGTH: 19
<212> TYPE: DNA
<213> ORGANISM: Artificial
<220> FEATURE:
<223> OTHER INFORMATION: Synthetic oligonucleotide

<400> SEQUENCE: 34
cagattgaga taaagaagt                                                    19

<210> SEQ ID NO 35
<211> LENGTH: 19
<212> TYPE: DNA
<213> ORGANISM: Artificial
<220> FEATURE:
<223> OTHER INFORMATION: Synthetic oligonucleotide

<400> SEQUENCE: 35
gagataaaga agttcaagt                                                    19

<210> SEQ ID NO 36
<211> LENGTH: 19
<212> TYPE: DNA
<213> ORGANISM: Artificial
<220> FEATURE:
<223> OTHER INFORMATION: Synthetic oligonucleotide

<400> SEQUENCE: 36
gataaagaag ttcaagtac                                                    19

<210> SEQ ID NO 37
<211> LENGTH: 19
<212> TYPE: DNA
<213> ORGANISM: Artificial
<220> FEATURE:
<223> OTHER INFORMATION: Synthetic oligonucleotide

<400> SEQUENCE: 37
aagaagttca agtacggta                                                    19

```
<210> SEQ ID NO 38
<211> LENGTH: 19
<212> TYPE: DNA
<213> ORGANISM: Artificial
<220> FEATURE:
<223> OTHER INFORMATION: Synthetic oligonucleotide

<400> SEQUENCE: 38
agaagttcaa gtacggtat                                                  19

<210> SEQ ID NO 39
<211> LENGTH: 19
<212> TYPE: DNA
<213> ORGANISM: Artificial
<220> FEATURE:
<223> OTHER INFORMATION: Synthetic oligonucleotide

<400> SEQUENCE: 39
gtacggtatt gaagagcat                                                  19

<210> SEQ ID NO 40
<211> LENGTH: 19
<212> TYPE: DNA
<213> ORGANISM: Artificial
<220> FEATURE:
<223> OTHER INFORMATION: Synthetic oligonucleotide

<400> SEQUENCE: 40
agagcatggt aaggtgaaa                                                  19

<210> SEQ ID NO 41
<211> LENGTH: 19
<212> TYPE: DNA
<213> ORGANISM: Artificial
<220> FEATURE:
<223> OTHER INFORMATION: Synthetic oligonucleotide

<400> SEQUENCE: 41
tgctgcgaac ctacatcat                                                  19

<210> SEQ ID NO 42
<211> LENGTH: 19
<212> TYPE: DNA
<213> ORGANISM: Artificial
<220> FEATURE:
<223> OTHER INFORMATION: Synthetic oligonucleotide

<400> SEQUENCE: 42
ctgcgaacct acatcatca                                                  19

<210> SEQ ID NO 43
<211> LENGTH: 19
<212> TYPE: DNA
<213> ORGANISM: Artificial
<220> FEATURE:
<223> OTHER INFORMATION: Synthetic oligonucleotide

<400> SEQUENCE: 43
gaacctacat catcagtat                                                  19

<210> SEQ ID NO 44
<211> LENGTH: 19
<212> TYPE: DNA
<213> ORGANISM: Artificial
<220> FEATURE:
<223> OTHER INFORMATION: Synthetic oligonucleotide
```

<400> SEQUENCE: 44
ttgctgatcc agtggtaca                                    19

<210> SEQ ID NO 45
<211> LENGTH: 19
<212> TYPE: DNA
<213> ORGANISM: Artificial
<220> FEATURE:
<223> OTHER INFORMATION: Synthetic oligonucleotide

<400> SEQUENCE: 45
tgatccagtg gtacatcta                                    19

<210> SEQ ID NO 46
<211> LENGTH: 19
<212> TYPE: DNA
<213> ORGANISM: Artificial
<220> FEATURE:
<223> OTHER INFORMATION: Synthetic oligonucleotide

<400> SEQUENCE: 46
agtggtacat ctatggatt                                    19

<210> SEQ ID NO 47
<211> LENGTH: 19
<212> TYPE: DNA
<213> ORGANISM: Artificial
<220> FEATURE:
<223> OTHER INFORMATION: Synthetic oligonucleotide

<400> SEQUENCE: 47
tcagcttgag tgctgttta                                    19

<210> SEQ ID NO 48
<211> LENGTH: 19
<212> TYPE: DNA
<213> ORGANISM: Artificial
<220> FEATURE:
<223> OTHER INFORMATION: Synthetic oligonucleotide

<400> SEQUENCE: 48
gagaaaacca tcttcatca                                    19

<210> SEQ ID NO 49
<211> LENGTH: 19
<212> TYPE: DNA
<213> ORGANISM: Artificial
<220> FEATURE:
<223> OTHER INFORMATION: Synthetic oligonucleotide

<400> SEQUENCE: 49
tgtccctggc cttgaatat                                    19

<210> SEQ ID NO 50
<211> LENGTH: 19
<212> TYPE: DNA
<213> ORGANISM: Artificial
<220> FEATURE:
<223> OTHER INFORMATION: Synthetic oligonucleotide

<400> SEQUENCE: 50
ccttgaatat cattgaact                                    19

<210> SEQ ID NO 51
<211> LENGTH: 19

<212> TYPE: DNA
<213> ORGANISM: Artificial
<220> FEATURE:
<223> OTHER INFORMATION: Synthetic oligonucleotide

<400> SEQUENCE: 51
cttcaagggc gttaaggat                                           19

<210> SEQ ID NO 52
<211> LENGTH: 19
<212> TYPE: DNA
<213> ORGANISM: Artificial
<220> FEATURE:
<223> OTHER INFORMATION: Synthetic oligonucleotide

<400> SEQUENCE: 52
gggttaaggg aaagagcga                                           19

<210> SEQ ID NO 53
<211> LENGTH: 19
<212> TYPE: DNA
<213> ORGANISM: Artificial
<220> FEATURE:
<223> OTHER INFORMATION: Synthetic oligonucleotide

<400> SEQUENCE: 53
cctgggtaca agctggtta                                           19

<210> SEQ ID NO 54
<211> LENGTH: 19
<212> TYPE: DNA
<213> ORGANISM: Artificial
<220> FEATURE:
<223> OTHER INFORMATION: Synthetic oligonucleotide

<400> SEQUENCE: 54
tggttactgg cgacagaaa                                           19

<210> SEQ ID NO 55
<211> LENGTH: 19
<212> TYPE: DNA
<213> ORGANISM: Artificial
<220> FEATURE:
<223> OTHER INFORMATION: Synthetic oligonucleotide

<400> SEQUENCE: 55
gagcaaaact gggctaatt                                           19

<210> SEQ ID NO 56
<211> LENGTH: 19
<212> TYPE: DNA
<213> ORGANISM: Artificial
<220> FEATURE:
<223> OTHER INFORMATION: Synthetic oligonucleotide

<400> SEQUENCE: 56
ggctaattac agtgcagaa                                           19

<210> SEQ ID NO 57
<211> LENGTH: 19
<212> TYPE: DNA
<213> ORGANISM: Artificial
<220> FEATURE:
<223> OTHER INFORMATION: Synthetic oligonucleotide

<400> SEQUENCE: 57
ctaattacag tgcagaaca                                              19

<210> SEQ ID NO 58
<211> LENGTH: 19
<212> TYPE: DNA
<213> ORGANISM: Artificial
<220> FEATURE:
<223> OTHER INFORMATION: Synthetic oligonucleotide

<400> SEQUENCE: 58
taattacagt gcagaacaa                                              19

<210> SEQ ID NO 59
<211> LENGTH: 19
<212> TYPE: DNA
<213> ORGANISM: Artificial
<220> FEATURE:
<223> OTHER INFORMATION: Synthetic oligonucleotide

<400> SEQUENCE: 59
gtgcagaaca aaatcgaat                                              19

<210> SEQ ID NO 60
<211> LENGTH: 19
<212> TYPE: DNA
<213> ORGANISM: Artificial
<220> FEATURE:
<223> OTHER INFORMATION: Synthetic oligonucleotide

<400> SEQUENCE: 60
gcgggaagca ccatctcta                                              19

<210> SEQ ID NO 61
<211> LENGTH: 19
<212> TYPE: DNA
<213> ORGANISM: Artificial
<220> FEATURE:
<223> OTHER INFORMATION: Synthetic oligonucleotide

<400> SEQUENCE: 61
cgggaagcac catctctaa                                              19

<210> SEQ ID NO 62
<211> LENGTH: 19
<212> TYPE: DNA
<213> ORGANISM: Artificial
<220> FEATURE:
<223> OTHER INFORMATION: Synthetic oligonucleotide

<400> SEQUENCE: 62
ccgatgataa ccagaattc                                              19

<210> SEQ ID NO 63
<211> LENGTH: 19
<212> TYPE: DNA
<213> ORGANISM: Artificial
<220> FEATURE:
<223> OTHER INFORMATION: Synthetic oligonucleotide

<400> SEQUENCE: 63
aaaactagct gctggacat                                              19

<210> SEQ ID NO 64
<211> LENGTH: 19
<212> TYPE: DNA
<213> ORGANISM: Artificial

```
<220> FEATURE:
<223> OTHER INFORMATION: Synthetic oligonucleotide

<400> SEQUENCE: 64
actagctgct ggacatgaa                                                    19

<210> SEQ ID NO 65
<211> LENGTH: 19
<212> TYPE: DNA
<213> ORGANISM: Artificial
<220> FEATURE:
<223> OTHER INFORMATION: Synthetic oligonucleotide

<400> SEQUENCE: 65
gtggaccagc gaccttcaa                                                    19

<210> SEQ ID NO 66
<211> LENGTH: 19
<212> TYPE: DNA
<213> ORGANISM: Artificial
<220> FEATURE:
<223> OTHER INFORMATION: Synthetic oligonucleotide

<400> SEQUENCE: 66
ccagcgacct tcaagcaga                                                    19

<210> SEQ ID NO 67
<211> LENGTH: 19
<212> TYPE: DNA
<213> ORGANISM: Artificial
<220> FEATURE:
<223> OTHER INFORMATION: Synthetic oligonucleotide

<400> SEQUENCE: 67
cgaccttcaa gcagagcca                                                    19

<210> SEQ ID NO 68
<211> LENGTH: 19
<212> TYPE: DNA
<213> ORGANISM: Artificial
<220> FEATURE:
<223> OTHER INFORMATION: Synthetic oligonucleotide

<400> SEQUENCE: 68
ggcctgatga cctggagat                                                    19

<210> SEQ ID NO 69
<211> LENGTH: 19
<212> TYPE: DNA
<213> ORGANISM: Artificial
<220> FEATURE:
<223> OTHER INFORMATION: Synthetic oligonucleotide

<400> SEQUENCE: 69
ctgatgacct ggagatcta                                                    19

<210> SEQ ID NO 70
<211> LENGTH: 19
<212> TYPE: DNA
<213> ORGANISM: Artificial
<220> FEATURE:
<223> OTHER INFORMATION: Synthetic oligonucleotide

<400> SEQUENCE: 70
gcatttgcaa atacgtata                                                    19
```

<210> SEQ ID NO 71
<211> LENGTH: 19
<212> TYPE: DNA
<213> ORGANISM: Artificial
<220> FEATURE:
<223> OTHER INFORMATION: Synthetic oligonucleotide

<400> SEQUENCE: 71
tccatccact tgcacaata                                              19

<210> SEQ ID NO 72
<211> LENGTH: 19
<212> TYPE: DNA
<213> ORGANISM: Artificial
<220> FEATURE:
<223> OTHER INFORMATION: Synthetic oligonucleotide

<400> SEQUENCE: 72
catcattcct cagctacta                                              19

<210> SEQ ID NO 73
<211> LENGTH: 19
<212> TYPE: DNA
<213> ORGANISM: Artificial
<220> FEATURE:
<223> OTHER INFORMATION: Synthetic oligonucleotide

<400> SEQUENCE: 73
ggaatcaagc catgcttaa                                              19

<210> SEQ ID NO 74
<211> LENGTH: 19
<212> TYPE: DNA
<213> ORGANISM: Artificial
<220> FEATURE:
<223> OTHER INFORMATION: Synthetic oligonucleotide

<400> SEQUENCE: 74
acaagcagat acagtataa                                              19

<210> SEQ ID NO 75
<211> LENGTH: 19
<212> TYPE: DNA
<213> ORGANISM: Artificial
<220> FEATURE:
<223> OTHER INFORMATION: Synthetic oligonucleotide

<400> SEQUENCE: 75
ttcctgctgt ggcaagtaa                                              19

<210> SEQ ID NO 76
<211> LENGTH: 19
<212> TYPE: DNA
<213> ORGANISM: Artificial
<220> FEATURE:
<223> OTHER INFORMATION: Synthetic oligonucleotide

<400> SEQUENCE: 76
tgcttagagt ggactatta                                              19

<210> SEQ ID NO 77
<211> LENGTH: 19
<212> TYPE: DNA
<213> ORGANISM: Artificial
<220> FEATURE:
<223> OTHER INFORMATION: Synthetic oligonucleotide

<400> SEQUENCE: 77
tgcaagagag gttgaaaga                                                19

<210> SEQ ID NO 78
<211> LENGTH: 19
<212> TYPE: DNA
<213> ORGANISM: Artificial
<220> FEATURE:
<223> OTHER INFORMATION: Synthetic oligonucleotide

<400> SEQUENCE: 78
tcagcttcat tgcatgtaa                                                19

<210> SEQ ID NO 79
<211> LENGTH: 16
<212> TYPE: DNA
<213> ORGANISM: Artificial
<220> FEATURE:
<223> OTHER INFORMATION: Synthetic oligonucleotide

<400> SEQUENCE: 79
gagcaaaacg ggccaa                                                   16

<210> SEQ ID NO 80
<211> LENGTH: 15
<212> TYPE: DNA
<213> ORGANISM: Artificial
<220> FEATURE:
<223> OTHER INFORMATION: Synthetic oligonucleotide

<400> SEQUENCE: 80
cgagaaccac acaca                                                    15

<210> SEQ ID NO 81
<211> LENGTH: 3124
<212> TYPE: DNA
<213> ORGANISM: Bos taurus

<400> SEQUENCE: 81
gaagctttta cgaggtatca gcacttttct ttcattaggg ggaaggagtg aggaaagtac    60
caaacagcag cagactttta aactttaaat agacaggtct gagtgcctgg gcttgctttt   120
tcatctttct tcatcctctg aggagttcaa tcacttggct tgcctacttc acttctttta   180
agagaaagag cagtacccag gcaacatggg tgactggagt gccttaggca aactccttga   240
caaggttcaa gcctactcca cggctggagg gaaggtgtgg ctgtcagtcc ttttcatttt   300
ccgaatcctg ctactgggga cagcggttga gtcagcctgg ggtgatgagc agtctgcctt   360

tcgttgtaac actcaacaac ctggttgtga aaatgtctgc tatgacaaat ccttcccaat   420
ctctcatgtg cgcttctggg tcctgcagat catatttgtg tctgttccca cactcctgta   480
cctggctcat gtgttctacg tgatgcgaaa ggaagagaag ctgaacaaga aggaggagga   540
actcaaagtt gttgcccaaa ctgatggtgc caacgtggac atgcacttga agcagattga   600
aattaagaag ttcaagtatg gcattgaaga gcacggcaag gtgaagatgc gagggggctt   660
gctgagaacc tacatcatca gtatcctctt caagtctgtc ttcgaggtgg ccttcttgct   720
gatccagtgg tacatctatg gttcagcttt gagtgccgtt tacacttgca aagagatcc   780 ctgcccacat caggtggact gtttcctttc tcggccacg gagaaaacca tcttcatcat   840
cttcatgctt gtcgtgtcat tggtgtctct tgccttgaac atcatcgaac tcttctatgt   900

```
cttcttcaag ggtgttaagg atcgtgtgaa gggaaagagc gatccttacc acactaccac    960
tggcccactg agcccctcca aagactgtgg atctccaaaa tatgcttatt tcaatggctg   1020
ctcctcccca accgctcctc tctcgcccat gtctcctccc gggtacaagc tggtcaccgg   1080
agacagaaac aattcttcct gccgcaatta caacaaacaa gcaagtgagc aaaactgggc   1140
caattacagc gcagaacaaa atcgaatggg gcaggcaggc agcaccatct ctaactccca   1200
cgcacagcct tttgatttcc cagacgacca ccagaattct aaaaagcttg atgctggcca   1260
cgaactacag cctctcgcca ttgtggacca gcggccttcc agcagagcca gcagtcgcgc   1320
cagcagccga ccccggcctg atgacctaga gatctaggtc cagttgagat cccactcagt   1380
tgtggagaag aaacaggtgc tataaaaaat gcaccttagg tgttcatttt gtttcattgg   1440
aggtggtact caacagcctt gccatgaggc ttagaaaaca caaagacatt agaatacctg   1500
gttcattggg ggtgttaggg ataggcgagt ggagagggag gggatgaggg aggtacatgt   1560
tggtatttaa tgtaggtgat tcaaacagct taagttctaa gtaaaagttg cattaggtga   1620
tccataggta agggctttt ctttcccaca caccccctaag aatagttctg tgtatgtgaa   1680
agagtcagtg atattttgg ttaaatattt ttttgttcta ccaagaaact gaaataagtt   1740
tgaccaggag aaaatccttt ctgaacattt tacttatctt tatcaagaaa aagacagagg   1800
attgtcttta tgtccctgct aaaaacattc cattgttaaa atttgcactt tgaaggtaag   1860
ctttgtaggc ctgaccctcc aggtgtcaat gaacttcgct actagatttt tttattcgtg   1920
gtatcagtta agagttcaga caaggcccac aaaagaagac tttccatgca tttgcaaatc   1980
tcagccagtt atctttacat tcttttttta cattcacttg catatagtat taccatcact   2040
ttgcatcatt cctcaactac tattcatatt cgtttaatga tttctataaa cattttagag   2100
acagttggga tatcacttaa catttttttga gttagagtca gggaagcaag ccatgctcaa   2160
tatttaacag tcacttgtct gtgaatgtgt gtggaagagt gttttatttg tcatgtattg   2220
gtacaagtag atgcagtata aactcacaaa cacagatttg aaaataatgc acacatggtg   2280
ttcaaatttg aacctttctc atggatttta tggtgtgggc caatatggtg tttacattat   2340
ataattcctg ctgtgcaaat aaagcacatt ttttttccct aagatatttt ttctccatgt   2400
atcctattaa ggatactggg ttttttttaa tttagattct ttttctcttt tctttctttt   2460
tttttttttt tttagaatat agcagtaatg ctattgctga aaggaatgat tttcttttc   2520
tgaaatataa tcattgatgc ttgaatgata gaattttagt actgtaaaca ggctttagta   2580
attaatgtga gagacttaga agaaatgctt agagtggact ctgaagtgtg cctaaatgaa   2640
ttttgcagta actggtattc ttggttttgt cctacttaat acacattcat tcagaatttg   2700
tattctattt tgagtttgac agtcttttgg agtaaccagc aactttgatg tttgcactaa   2760
gattttatct ggaatgcaag agaggttgaa agaggtttca gtagtgcaca tgtaactaat   2820
ttatttgaaa tttatcctaa agaaatctac cagtttcttc aaatgctgtt taaaaattca   2880
tcacagatga ttagtgaaaa tacaaaatat catactttc ttgttgcatg tcagctacat   2940
aaagagtttt gtacaatgag aaatactaat ttgtttgaca ttccatgtta aactgctgcc   3000
atgttcagct tcattgcatg taatgtagac ctagtccatc gatcatgtgt tctggagagt   3060
gttcttatt caataaagtt ttaatttagt ataaaaaaa aaaaaaaaa aaaaaaaaa   3120
aaaa                                                                3124
```

RNAI-MEDIATED INHIBITION OF CONNEXIN 43 FOR TREATMENT OF IOP-RELATED CONDITIONS

CROSS-REFERENCE TO RELATED APPLICATION

This application is a divisional of U.S. application Ser. No. 12/371,007, filed 13 Dec. 2009, which claims priority under 35 U.S.C. §119 to U.S. Provisional Patent Application No. 61/028,966 filed Feb. 15, 2008, the entire contents of which are incorporated herein by reference.

FIELD OF THE INVENTION

The present invention relates to the field of interfering RNA compositions for inhibition of expression of the protein connexin 43 (Cx43) in intraocular pressure (IOP)-related conditions such as ocular hypertension and glaucoma, including normal tension glaucoma and open angle glaucoma.

BACKGROUND OF THE INVENTION

Glaucoma is a heterogeneous group of optic neuropathies that share certain clinical features. The loss of vision in glaucoma is due to the selective death of retinal ganglion cells in the neural retina that is clinically diagnosed by characteristic changes in the visual field, nerve fiber layer defects, and a progressive cupping of the optic nerve head (ONH). One of the main risk factors for the development of glaucoma is the presence of ocular hypertension (elevated intraocular pressure). An adequate intraocular pressure is needed to maintain the shape of the eye and to provide a pressure gradient to allow for the flow of aqueous humor to the avascular cornea and lens. IOP levels may also be involved in the pathogenesis of normal tension glaucoma (NTG), as evidenced by patients benefiting from IOP lowering medications. Once adjustments for central corneal thickness are made to IOP readings in NTG patients, many of these patients may be found to be ocular hypertensive.

The elevated IOP associated with glaucoma is due to elevated aqueous humor outflow resistance in the trabecular meshwork (TM), a small specialized tissue located in the iris-corneal angle of the ocular anterior chamber. Glaucomatous changes to the TM include a loss in TM cells and the deposition and accumulation of extracellular debris including proteinaceous plaque-like material. In addition, there are also changes that occur in the glaucomatous ONH. In glaucomatous eyes, there are morphological and mobility changes in ONH glial cells. In response to elevated IOP and/or transient ischemic insults, there is a change in the composition of the ONH extracellular matrix and alterations in the glial cell and retinal ganglion cell axon morphologies.

Primary glaucomas result from disturbances in the flow of intraocular fluid that has an anatomical or physiological basis. Secondary glaucomas occur as a result of injury or trauma to the eye or a preexisting disease. Primary open angle glaucoma (POAG), also known as chronic or simple glaucoma, represents the majority of all primary glaucomas. POAG is characterized by the degeneration of the trabecular meshwork, resulting in abnormally high resistance to fluid drainage from the eye. A consequence of such resistance is an increase in the IOP that is required to drive the fluid normally produced by the eye across the increased resistance.

Current anti-glaucoma therapies include lowering IOP by the use of suppressants of aqueous humor formation or agents that enhance uveoscleral outflow, laser trabeculoplasty, or trabeculectomy, which is a filtration surgery to improve drainage. Pharmaceutical anti-glaucoma approaches have exhibited various undesirable side effects. For example, miotics such as pilocarpine can cause blurring of vision and other negative visual side effects. Systemically administered carbonic anhydrase inhibitors (CAis) can also cause nausea, dyspepsia, fatigue, and metabolic acidosis. Further, certain beta-blockers have increasingly become associated with serious pulmonary side effects attributable to their effects on beta-2 receptors in pulmonary tissue. Sympathomimetics cause tachycardia, arrhythmia and hypertension. Such negative side effects may lead to decreased patient compliance or to termination of therapy. In addition, the efficacy of current IOP lowering therapies is relatively short-lived requiring repeated dosing during each day and, in some cases, the efficacy decreases with time.

In view of the importance of ocular hypertension in glaucoma, and the inadequacies of prior methods of treatment, it would be desirable to have an improved method of treating ocular hypertension that would address the underlying causes of its progression.

SUMMARY OF THE INVENTION

The invention provides interfering RNAs that silence connexin 43 (Cx43) mRNA expression, thereby reducing production of aqueous humor in a subject. Thus, silencing Cx43 mRNA expression results in the lowering of intraocular pressure in patients with IOP-related conditions. The interfering RNAs of the invention are useful for treating patients with IOP-related conditions, including ocular hypertension and glaucoma, such as normal tension glaucoma and open angle glaucoma.

The invention also provides a method of attenuating expression of a Cx43 mRNA in a subject. In one aspect, the method comprises administering to the subject a composition comprising an effective amount of interfering RNA having a length of 19 to 49 nucleotides and a pharmaceutically acceptable carrier. In another aspect, administration is to an eye of the subject for attenuating expression of Cx43 in a human.

In one aspect, the invention provides a method of attenuating expression of Cx43 mRNA in an eye of a subject, comprising administering to the eye of the subject an interfering RNA that comprises a region that can recognize a portion of mRNA corresponding to SEQ ID NO: 1, which is the sense cDNA sequence encoding Cx43 (GenBank Accession No. NM_000165), wherein the expression of Cx43 mRNA is attenuated thereby. In addition, the invention provides methods of treating an TOP-related condition in a subject in need thereof, comprising administering to the eye of the subject an interfering RNA that comprises a region that can recognize a portion of mRNA corresponding to a portion of SEQ ID NO: 1, wherein the expression of Cx43 mRNA is attenuated thereby.

In certain aspects, an interfering RNA of the invention is designed to target an mRNA corresponding to a portion of SEQ ID NO: 1, wherein the portion comprises nucleotide 227, 267, 270, 395, 446, 447, 480, 555, 557, 560, 561, 586, 598, 618, 620, 621, 626, 627, 628, 630, 632, 634, 635, 641, 643, 647, 648, 658, 670, 702, 704, 708, 758, 762, 768, 786, 863, 906, 915, 946, 966, 1100, 1113, 1169, 1180, 1182, 1183, 1191, 1217, 1218, 1263, 1285, 1288, 1325, 1330, 1334, 1377, 1380, 2021, 2047, 2084, 2186, 2263, 2386, 2632, 2800, or 3035 of SEQ ID NO: 1. In particular aspects, a "portion of SEQ ID NO: 1" is about 19 to about 49 nucleotides in length.

In certain aspects, an interfering RNA of the invention has a length of about 19 to about 49 nucleotides. In other aspects, the interfering RNA comprises a sense nucleotide strand and an antisense nucleotide strand, wherein each strand has a region of at least near-perfect contiguous complementarity of at least 19 nucleotides with the other strand, and wherein the antisense strand can recognize a portion of Cx43 mRNA corresponding to a portion of SEQ ID NO: 1, and has a region of at least near-perfect contiguous complementarity of at least 19 nucleotides with the portion of Cx43 mRNA. The sense and antisense strands can be connected by a linker sequence, which allows the sense and antisense strands to hybridize to each other thereby forming a hairpin loop structure as described herein.

In still other aspects, an interfering RNA of the invention is a single-stranded interfering RNA, and wherein single-stranded interfering RNA recognizes a portion of mRNA corresponding to a portion of SEQ ID NO: 1. In certain aspects, the interfering RNA has a region of at least near-perfect contiguous complementarity of at least 19 nucleotides with the portion of mRNA corresponding to the portion of SEQ ID NO: 1. In other aspects, the portion of SEQ ID NO: 1 comprises 227, 267, 270, 395, 446, 447, 480, 555, 557, 560, 561, 586, 598, 618, 620, 621, 626, 627, 628, 630, 632, 634, 635, 641, 643, 647, 648, 658, 670, 702, 704, 708, 758, 762, 768, 786, 863, 906, 915, 946, 966, 1100, 1113, 1169, 1180, 1182, 1183, 1191, 1217, 1218, 1263, 1285, 1288, 1325, 1330, 1334, 1377, 1380, 2021, 2047, 2084, 2186, 2263, 2386, 2632, 2800, or 3035 of SEQ ID NO: 1.

In still other aspects, an interfering RNA of the invention comprises: (a) a region of at least 13 contiguous nucleotides having at least 90% sequence complementarity to, or at least 90% sequence identity with, the penultimate 13 nucleotides of the 3' end of a mRNA corresponding to any one of SEQ ID NO: 2, and SEQ ID NO:13-SEQ ID NO: 80; (b) a region of at least 14 contiguous nucleotides having at least 85% sequence complementarity to, or at least 85% sequence identity with, the penultimate 14 nucleotides of the 3' end of an mRNA corresponding to any one of SEQ ID NO: 2, and SEQ ID NO: 13-SEQ ID NO: 80; or (c) a region of at least 15, 16, 17, or 18 contiguous nucleotides having at least 80% sequence complementarity to, or at least 80% sequence identity with, the penultimate 15, 16, 17, or 18 nucleotides, respectively, of the 3' end of an mRNA corresponding to any one of SEQ ID NO: 2, and SEQ ID NO: 13-SEQ ID NO: 80; wherein the expression of the Cx43 mRNA is attenuated thereby.

In further aspects, an interfering RNA of the invention or composition comprising an interfering RNA of the invention is administered to a subject via a topical, intravitreal, transcleral, periocular, conjunctival, subtenon, intracameral, subretinal, subconjunctival, retrobulbar, or intracanalicular route.

The interfering RNA or composition can be administered, for example, via in vivo expression from an interfering RNA expression vector. In certain aspects, the interfering RNA or composition can be administered via an aerosol, buccal, dermal, intradermal, inhaling, intramuscular, intranasal, intraocular, intrapulmonary, intravenous, intraperitoneal, nasal, ocular, oral, otic, parenteral, patch, subcutaneous, sublingual, topical, or transdermal route.

In one aspect, an interfering RNA molecule of the invention is isolated. The term "isolated" means that the interfering RNA is free of its total natural milieu.

The invention further provides methods of treating an IOP-related condition in a subject in need thereof, comprising administering to the subject a composition comprising a double-stranded siRNA molecule that down regulates expression of a Cx43 gene via RNA interference, wherein each strand of the siRNA molecule is independently about 19 to about 27 nucleotides in length, and one strand of the siRNA molecule comprises a nucleotide sequence having substantial complementarity to an mRNA corresponding to the Cx43 gene so that the siRNA molecule directs cleavage of the mRNA via RNA interference. In certain aspects, the siRNA molecule is administered via an aerosol, buccal, dermal, intradermal, inhaling, intramuscular, intranasal, intraocular, intrapulmonary, intravenous, intraperitoneal, nasal, ocular, oral, otic, parenteral, patch, subcutaneous, sublingual, topical, or transdermal route.

The invention further provides for administering a second interfering RNA to a subject in addition to a first interfering RNA. The second interfering RNA may target the same mRNA target gene as the first interfering RNA or may target a different gene. Further, a third, fourth, or fifth, etc. interfering RNA may be administered in a similar manner.

Use of any of the embodiments as described herein in the preparation of a medicament for attenuating expression of Cx43 mRNA is also an embodiment of the present invention.

Specific preferred embodiments of the invention will become evident from the following more detailed description of certain preferred embodiments and the claims.

BRIEF DESCRIPTION OF THE DRAWINGS

FIG. 1 provides results of a western blot analysis of bovine Cx43 protein expression in CPA-47 cells transfected with bovine Cx43 siRNAs #1, #2, #3, and #4, each at 10 nM, 1 nM, and 0.1 nM.

DETAILED DESCRIPTION OF THE INVENTION

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

The following definitions and explanations are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3rd Edition or a dictionary known to those of skill in the art, such as the Oxford Dictionary of Biochemistry and Molecular Biology (Ed. Anthony Smith, Oxford University Press, Oxford, 2004).

As used herein, all percentages are percentages by weight, unless stated otherwise.

As used herein and unless otherwise indicated, the terms "a" and "an" are taken to mean "one", "at least one" or "one or more". Unless otherwise required by context, singular terms used herein shall include pluralities and plural terms shall include the singular.

In certain embodiments, the invention provides methods that comprise the use of interfering RNA to inhibit the expression of connexin 43 (Cx43) mRNA. Cx43, also known as Gap Junction Protein, Alpha-1 (GJA1), is a member of a family of proteins, the "connexins," which comprise the building blocks of gap junctions. Gap junctions are large aggregates of intercellular channels that connect the cytoplasm of adjacent cells. These channels allow small molecules of up to approximately 1 kD to diffuse between cells. The channels are assembled from subunit proteins called "connexins." Connexins oligomerize to form homomeric or heteromeric "connexons" (i.e. hexameric hemichannels that span the plasma membrane). Connexons on adjacent cells interact to form homotypic or heterotypic intercellular channels, which associate laterally with up to 105 other connexons to form gap junctions. Gap junctions have a wide variety of functions, including rapid propagation of excitation events in muscle and central nervous system (CNS) and "diffusional feeding" in avascular tissues.

In the eye, homomeric/homotypic Cx43 channels connect the pigmented epithelial (PE) and non-pigmented epithelial (NPE) cells of the ciliary body (Coffey et al., 2002, *Exp. Eye Res.*75:9-21). Coupling enables these two cell layers to function as a syncitium. It has been proposed that PE/NPE coupling via gap junctions is required for production of aqueous humor, and that modulation of this coupling may represent a novel target for reduction of intraocular pressure (TOP) (Stelling and Jacob, 1997, *Am. J. Physiol.* 273: C1876-C1881; Wolosin et al., 1997, *Exp. Eye Res.* 64:945-952). Analysis of Cx43-deficient mice further supports the proposed role of Cx43 in aqueous humor production (Calera et al., 2006, *J. Cell Sci.* 119:4510-4519). Therefore, silencing Cx43 expression with one or more of the Cx43 siRNAs of the invention as provided herein is an effective method of lowering IOP in the treatment of ocular disease related to ocular hypertension and/or glaucoma.

According to the present invention, inhibiting the expression of Cx43 mRNA effectively reduces the action of Cx43. Further, interfering RNAs as set forth herein provided exogenously or expressed endogenously are particularly effective at silencing Cx43 mRNA.

RNA interference (RNAi) is a process by which double-stranded RNA (dsRNA) is used to silence gene expression. While not wanting to be bound by theory, RNAi begins with the cleavage of longer dsRNAs into small interfering RNAs (siRNAs) by an RNaseIII-like enzyme, dicer. SiRNAs are dsRNAs that are usually about 19 to 28 nucleotides, or 20 to 25 nucleotides, or 21 to 22 nucleotides in length and often contain 2-nucleotide 3' overhangs, and 5' phosphate and 3' hydroxyl termini. One strand of the siRNA is incorporated into a ribonucleoprotein complex known as the RNA-induced silencing complex (RISC). RISC uses this siRNA strand to identify mRNA molecules that are at least partially complementary to the incorporated siRNA strand, and then cleaves these target mRNAs or inhibits their translation. Therefore, the siRNA strand that is incorporated into RISC is known as the guide strand or the antisense strand. The other siRNA strand, known as the passenger strand or the sense strand, is eliminated from the siRNA and is at least partially homologous to the target mRNA. Those of skill in the art will recognize that, in principle, either strand of an siRNA can be incorporated into RISC and function as a guide strand. However, siRNA design (e.g., decreased siRNA duplex stability at the 5' end of the desired guide strand) can favor incorporation of the desired guide strand into RISC.

The antisense strand of an siRNA is the active guiding agent of the siRNA in that the antisense strand is incorporated into RISC, thus allowing RISC to identify target mRNAs with at least partial complementarity to the antisense siRNA strand for cleavage or translational repression. RISC-mediated cleavage of mRNAs having a sequence at least partially complementary to the guide strand leads to a decrease in the steady state level of that mRNA and of the corresponding protein encoded by this mRNA. Alternatively, RISC can also decrease expression of the corresponding protein via translational repression without cleavage of the target mRNA.

Interfering RNAs of the invention appear to act in a catalytic manner for cleavage of target mRNA, i.e., interfering RNA is able to effect inhibition of target mRNA in substoichiometric amounts. As compared to antisense therapies, significantly less interfering RNA is required to provide a therapeutic effect under such cleavage conditions.

In certain embodiments, the invention provides methods of using interfering RNA to inhibit the expression of Cx43 target mRNA thus decreasing Cx43 levels (i.e. reduce Cx43 protein expression) in patients with an IOP-related condition. According to the present invention, interfering RNAs provided exogenously or expressed endogenously effect silencing of Cx43 expression in ocular tissues.

The phrase, "attenuating expression of an mRNA," as used herein, means administering or expressing an amount of interfering RNA (e.g., an siRNA) to reduce translation of the target mRNA into protein, either through mRNA cleavage or through direct inhibition of translation. The terms "inhibit," "silencing," and "attenuating" as used herein refer to a measurable reduction in expression of a target mRNA or the corresponding protein as compared with the expression of the target mRNA or the corresponding protein in the absence of an interfering RNA of the invention. The reduction in expression of the target mRNA or the corresponding protein is commonly referred to as "knock-down" and is reported relative to levels present in non-transfected cells or in cells that have been transfected with a control RNA (e.g., a non-targeting control siRNA). Knock-down of expression of an amount including and between 50% and 100% is contemplated by embodiments herein. However, it is not necessary that such knock-down levels be achieved for purposes of the present invention.

Knock-down is commonly assessed by measuring the mRNA levels using quantitative polymerase chain reaction (qPCR) amplification or by measuring protein levels by western blot or enzyme-linked immunosorbent assay (ELISA). Analyzing the protein level provides an assessment of both mRNA cleavage as well as translation inhibition. Further techniques for measuring knock-down include RNA solution hybridization, nuclease protection, northern hybridization, gene expression monitoring with a microarray, antibody binding, radioimmunoassay, and fluorescence activated cell analysis.

Attenuating expression of Cx43 by an interfering RNA molecule of the invention can be inferred in a human or other mammal by observing an improvement in an TOP-related symptom such as improvement in intraocular pressure, improvement in visual field loss, or improvement in optic nerve head changes, for example.

The ability of interfering RNA to knock-down the levels of endogenous target gene expression in, for example, HeLa cells can be evaluated in vitro as follows. HeLa cells are plated 24 h prior to transfection in standard growth medium (e.g., DMEM supplemented with 10% fetal bovine serum). Transfection is performed using, for example, Dharmafect 1 (Dharmacon, Lafayette, Colo.) according to the manufacturer's instructions at interfering RNA concentrations ranging from 0.1 nM-100 nM. siCONTROL™ Non-Targeting siRNA #1 and siCONTROL™ Cyclophilin B siRNA (Dharmacon) are used as negative and positive controls, respectively. Target mRNA levels and cyclophilin B mRNA (PPIB, NM_000942) levels are assessed by qPCR 24 h post-transfection using, for example, a TAQMAN® Gene Expression Assay that preferably overlaps the target site (Applied Biosystems, Foster City, Calif.). The positive control siRNA gives essentially complete knockdown of cyclophilin B mRNA when transfection efficiency is 100%. Therefore, target mRNA knockdown is corrected for transfection efficiency by reference to the cyclophilin B mRNA level in cells transfected with the cyclophilin B siRNA. Target protein levels may be assessed approximately 72 h post-transfection (actual time dependent on protein turnover rate) by western blot, for example. Standard techniques for RNA and/or protein isolation from cultured cells are well-known to those skilled in the art. To reduce the chance of non-specific, off-target effects, the lowest possible concentration of interfering RNA is used that produces the desired level of knock-down in target gene expression. Human corneal epithelial cells or other human ocular cell lines may also be used for an evaluation of the ability of interfering RNA to knock-down levels of an endogenous target gene.

In one embodiment, a single interfering RNA targeting Cx43 mRNA is administered to decrease Cx43 levels (i.e. reduce Cx43 protein expression in a cell). In other embodiments, two or more interfering RNAs targeting the Cx43 mRNA are administered to decrease Cx43 levels.

The GenBank database provides the DNA sequence for Cx43 as accession no. NM_000165 (SEQ ID NO: 1). SEQ ID NO: 1 provides the sense strand sequence of DNA that corresponds to the mRNA encoding Cx43 (with the exception of "T" bases for "U" bases). The coding sequence for Cx43 is from nucleotides 235-3130.

Equivalents of the above cited Cx43 mRNA sequence are alternative splice forms, allelic forms, isozymes, or a cognate thereof. A cognate is a Cx43 mRNA from another mammalian species that is homologous to SEQ ID NO: 1 (i.e., an ortholog).

In certain embodiments, a "subject" in need of treatment for an IOP-related condition or at risk for developing an IOP-related condition is a human or other mammal having an IOP-related condition or at risk of having an IOP-related condition associated with undesired or inappropriate expression or activity of Cx43. Ocular structures associated with such disorders may include the eye, retina, choroid, lens, cornea, trabecular meshwork, iris, optic nerve, optic nerve head, sclera, anterior or posterior segment, or ciliary body, for example. A subject may also be an ocular cell, cell culture, organ or an ex vivo organ or tissue or cell.

An "IOP-related condition," as used herein, includes ocular hypertension and ocular diseases associated with elevated intraocular pressure (TOP), such as glaucoma, including normal tension glaucoma and open angle glaucoma.

The term "siRNA" as used herein refers to a double-stranded interfering RNA unless otherwise noted. Typically, an siRNA of the invention is a double-stranded nucleic acid molecule comprising two nucleotide strands, each strand having about 19 to about 28 nucleotides (i.e. about 19, 20, 21, 22, 23, 24, 25, 26, 27, or 28 nucleotides). The phrase "interfering RNA having a length of 19 to 49 nucleotides" when referring to a double-stranded interfering RNA means that the antisense and sense strands independently have a length of about 19 to about 49 nucleotides, including interfering RNA molecules where the sense and antisense strands are connected by a linker molecule.

In addition to siRNA molecules, other interfering RNA molecules and RNA-like molecules can interact with RISC and silence gene expression. Examples of other interfering RNA molecules that can interact with RISC include short hairpin RNAs (shRNAs), single-stranded siRNAs, microRNAs (miRNAs), and dicer-substrate 27-mer duplexes. Examples of RNA-like molecules that can interact with RISC include siRNA, single-stranded siRNA, microRNA, and shRNA molecules containing one or more chemically modified nucleotides, one or more non-nucleotides, one or more deoxyribonucleotides, and/or one or more non-phosphodiester linkages. All RNA or RNA-like molecules that can interact with RISC and participate in RISC-mediated changes in gene expression are referred to herein as "interfering RNAs" or "interfering RNA molecules." SiRNAs, single-stranded siRNAs, shRNAs, miRNAs, and dicer-substrate 27-mer duplexes are, therefore, subsets of "interfering RNAs" or "interfering RNA molecules."

Single-stranded interfering RNA has been found to effect mRNA silencing, albeit less efficiently than double-stranded RNA. Therefore, embodiments of the present invention also provide for administration of a single-stranded interfering RNA that has a region of at least near-perfect contiguous complementarity with a portion of SEQ ID NO: 1. The single-stranded interfering RNA has a length of about 19 to about 49 nucleotides as for the double-stranded interfering RNA cited above. The single-stranded interfering RNA has a 5' phosphate or is phosphorylated in situ or in vivo at the 5' position. The term "5' phosphorylated" is used to describe, for example, polynucleotides or oligonucleotides having a phosphate group attached via ester linkage to the C5 hydroxyl of the sugar (e.g., ribose, deoxyribose, or an analog of same) at the 5' end of the polynucleotide or oligonucleotide.

Single-stranded interfering RNAs can be synthesized chemically or by in vitro transcription or expressed endogenously from vectors or expression cassettes as described herein in reference to double-stranded interfering RNAs. 5' Phosphate groups may be added via a kinase, or a 5' phosphate may be the result of nuclease cleavage of an RNA. A hairpin interfering RNA is a single molecule (e.g., a single oligonucleotide chain) that comprises both the sense and antisense strands of an interfering RNA in a stem-loop or hairpin structure (e.g., a shRNA). For example, shRNAs can be expressed from DNA vectors in which the DNA oligonucleotides encoding a sense interfering RNA strand are linked to the DNA oligonucleotides encoding the reverse complementary antisense interfering RNA strand by a short spacer. If needed for the chosen expression vector, 3' terminal T's and nucleotides forming restriction sites may be added. The resulting RNA transcript folds back onto itself to form a stem-loop structure.

Nucleic acid sequences cited herein are written in a 5' to 3' direction unless indicated otherwise. The term "nucleic acid," as used herein, refers to either DNA or RNA or a modified form thereof comprising the purine or pyrimidine bases present in DNA (adenine "A," cytosine "C," guanine "G," thymine "T") or in RNA (adenine "A," cytosine "C," guanine "G," uracil "U"). Interfering RNAs provided herein may comprise "T" bases, particularly at 3' ends, even though "T" bases do not naturally occur in RNA. "Nucleic acid"

includes the terms "oligonucleotide" and "polynucleotide" and can refer to a single-stranded molecule or a double-stranded molecule. A double-stranded molecule is formed by Watson-Crick base pairing between A and T bases, C and G bases, and between A and U bases. The strands of a double-stranded molecule may have partial, substantial or full complementarity to each other and will form a duplex hybrid, the strength of bonding of which is dependent upon the nature and degree of complementarity of the sequence of bases.

The phrase "DNA target sequence" as used herein refers to the DNA sequence that is used to derive an interfering RNA of the invention. The phrases "RNA target sequence," "interfering RNA target sequence," and "RNA target" as used herein refer to the Cx43 mRNA or the portion of the Cx43 mRNA sequence that can be recognized by an interfering RNA of the invention, whereby the interfering RNA can silence Cx43 gene expression as discussed herein. An "RNA target sequence," an "siRNA target sequence," and an "RNA target" are typically mRNA sequences that correspond to a portion of a DNA sequence. An mRNA sequence is readily deduced from the sequence of the corresponding DNA sequence. For example, SEQ ID NO: 1 provides the sense strand sequence of DNA corresponding to the mRNA for Cx43. The mRNA sequence is identical to the DNA sense strand sequence with the "T" bases replaced with "U" bases. Therefore, the mRNA sequence of Cx43 is known from SEQ ID NO: 1. A target sequence in the mRNAs corresponding to SEQ ID NO: 1 may be in the 5' or 3' untranslated regions of the mRNA as well as in the coding region of the mRNA.

In certain embodiments, interfering RNA target sequences (e.g., siRNA target sequences) within a target mRNA sequence are selected using available design tools. Interfering RNAs corresponding to a Cx43 target sequence are then tested in vitro by transfection of cells expressing the target mRNA followed by assessment of knockdown as described herein. The interfering RNAs can be further evaluated in vivo using animal models as described herein.

Techniques for selecting target sequences for siRNAs are provided, for example, by Tuschl, T. et al., "The siRNA User Guide," revised May 6, 2004, available on the Rockefeller University web site; by Technical Bulletin #506, "siRNA Design Guidelines," Ambion Inc. at Ambion's web site; and by other web-based design tools at, for example, the Invitrogen, Dharmacon, Integrated DNA Technologies, or Genscript web sites.

Initial search parameters can include G/C contents between 35% and 55% and siRNA lengths between 19 and 27 nucleotides. The target sequence may be located in the coding region or in the 5' or 3' untranslated regions of the mRNA. The target sequences can be used to derive interfering RNA molecules, such as those described herein.

Table 1 lists examples of Cx43 DNA target sequences of SEQ ID NO: 1 from which siRNAs of the present invention are designed in a manner as set forth above. Cx43 encodes connexin 43, as noted above.

TABLE 1

Cx43 Target Sequences for siRNAs

| Cx43 Target Sequences | # of Starting Nucleotide with reference to SEQ ID NO: 1 | SEQ ID NO: |
|---|---|---|
| TAGGCAAACTCCTTGACAA | 227 | 2 |
| CCTTAGGCAAACTCCTTGA | 267 | 13 |

TABLE 1-continued

Cx43 Target Sequences for siRNAs

| Cx43 Target Sequences | # of Starting Nucleotide with reference to SEQ ID NO: 1 | SEQ ID NO: |
|---|---|---|
| TAGGCAAACTCCTTGACAA | 270 | 14 |
| CAGTCTGCCTTTCGTTGTA | 395 | 15 |
| TATGACAAGTCTTTCCCAA | 446 | 16 |
| ATGACAAGTCTTTCCCAAT | 447 | 17 |
| GTACCTGGCTCATGTGTTC | 480 | 18 |
| AGGAAGAGAAACTGAACAA | 555 | 19 |
| GAAGAGAAACTGAACAAGA | 557 | 20 |
| GAGAAACTGAACAAGAAAG | 560 | 21 |
| AGAAACTGAACAAGAAAGA | 561 | 22 |
| ACTCAAGGTTGCCCAAACT | 586 | 23 |
| CCAAACTGATGGTGTCAAT | 598 | 24 |
| TGGACATGCACTTGAAGCA | 618 | 25 |
| GACATGCACTTGAAGCAGA | 620 | 26 |
| ACATGCACTTGAAGCAGAT | 621 | 27 |
| CACTTGAAGCAGATTGAGA | 626 | 28 |
| ACTTGAAGCAGATTGAGAT | 627 | 29 |
| CTTGAAGCAGATTGAGATA | 628 | 30 |
| TGAAGCAGATTGAGATAAA | 630 | 31 |
| AAGCAGATTGAGATAAAGA | 632 | 32 |
| GCAGATTGAGATAAAGAAG | 634 | 33 |
| CAGATTGAGATAAAGAAGT | 635 | 34 |
| GAGATAAAGAAGTTCAAGT | 641 | 35 |
| GATAAAGAAGTTCAAGTAC | 643 | 36 |
| AAGAAGTTCAAGTACGGTA | 647 | 37 |
| AGAAGTTCAAGTACGGTAT | 648 | 38 |
| GTACGGTATTGAAGAGCAT | 658 | 39 |
| AGAGCATGGTAAGGTGAAA | 670 | 40 |
| TGCTGCGAACCTACATCAT | 702 | 41 |
| CTGCGAACCTACATCATCA | 704 | 42 |
| GAACCTACATCATCAGTAT | 708 | 43 |
| TTGCTGATCCAGTGGTACA | 758 | 44 |
| TGATCCAGTGGTACATCTA | 762 | 45 |
| AGTGGTACATCTATGGATT | 768 | 46 |
| TCAGCTTGAGTGCTGTTTA | 786 | 47 |
| GAGAAAACCATCTTCATCA | 863 | 48 |
| TGTCCCTGGCCTTGAATAT | 906 | 49 |
| CCTTGAATATCATTGAACT | 915 | 50 |

TABLE 1-continued

Cx43 Target Sequences for siRNAs

| Cx43 Target Sequences | # of Starting Nucleotide with reference to SEQ ID NO: 1 | SEQ ID NO: |
|---|---|---|
| CTTCAAGGGCGTTAAGGAT | 946 | 51 |
| GGGTTAAGGGAAAGAGCGA | 966 | 52 |
| CCTGGGTACAAGCTGGTTA | 1100 | 53 |
| TGGTTACTGGCGACAGAAA | 1113 | 54 |
| GAGCAAAACTGGGCTAATT | 1169 | 55 |
| GGCTAATTACAGTGCAGAA | 1180 | 56 |
| CTAATTACAGTGCAGAACA | 1182 | 57 |
| TAATTACAGTGCAGAACAA | 1183 | 58 |
| GTGCAGAACAAAATCGAAT | 1191 | 59 |
| GCGGGAAGCACCATCTCTA | 1217 | 60 |
| CGGGAAGCACCATCTCTAA | 1218 | 61 |
| CCGATGATAACCAGAATTC | 1263 | 62 |
| AAAACTAGCTGCTGGACAT | 1285 | 63 |
| ACTAGCTGCTGGACATGAA | 1288 | 64 |
| GTGGACCAGCGACCTTCAA | 1325 | 65 |
| CCAGCGACCTTCAAGCAGA | 1330 | 66 |
| CGACCTTCAAGCAGAGCCA | 1334 | 67 |
| GGCCTGATGACCTGGAGAT | 1377 | 68 |
| CTGATGACCTGGAGATCTA | 1380 | 69 |
| GCATTTGCAAATACGTATA | 2021 | 70 |
| TCCATCCACTTGCACAATA | 2047 | 71 |
| CATCATTCCTCAGCTACTA | 2084 | 72 |
| GGAATCAAGCCATGCTTAA | 2186 | 73 |
| ACAAGCAGATACAGTATAA | 2263 | 74 |
| TTCCTGCTGTGGCAAGTAA | 2386 | 75 |
| TGCTTAGAGTGGACTATTA | 2632 | 76 |
| TGCAAGAGAGGTTGAAAGA | 2800 | 77 |
| TCAGCTTCATTGCATGTAA | 3035 | 78 |

As cited in the examples above, one of skill in the art is able to use the target sequence information provided in Table 1 to design interfering RNAs having a length shorter or longer than the sequences provided in Table 1 by referring to the sequence position in SEQ ID NO: 1 and adding or deleting nucleotides complementary or near complementary to SEQ ID NO: 1.

For example, SEQ ID NO: 2 represents an example of a 19-nucleotide DNA target sequence for Cx43 mRNA is present at nucleotides 227 to 245 of SEQ ID NO: 1:

SEQ ID NO: 2
5'-TAGGCAAACTCCTTGACAA-3'.

An siRNA of the invention for targeting a corresponding mRNA sequence of SEQ ID NO: 2 and having 21-nucleotide strands and a 2-nucleotide 3' overhang is:

SEQ ID NO: 3
5'-UAGGCAAACUCCUUGACAANN-3'

SEQ ID NO: 4
3'-NNAUCCGUUUGAGGAACUGUU-5'.

Each "N" residue can be any nucleotide (A, C, G, U, T) or modified nucleotide. The 3' end can have a number of "N" residues between and including 1, 2, 3, 4, 5, and 6. The "N" residues on either strand can be the same residue (e.g., UU, AA, CC, GG, or TT) or they can be different (e.g., AC, AG, AU, CA, CG, CU, GA, GC, GU, UA, UC, or UG). The 3' overhangs can be the same or they can be different. In one embodiment, both strands have a 3'UU overhang.

An example of an siRNA of the invention for targeting a corresponding mRNA sequence of SEQ ID NO: 2 and having 21-nucleotide strands and a 3'UU overhang on each strand is:

SEQ ID NO: 5
5'-UAGGCAAACUCCUUGACAAUU-3'

SEQ ID NO: 6
3'-UUAUCCGUUUGAGGAACUGUU-5'.

The interfering RNA may also have a 5' overhang of nucleotides or it may have blunt ends. An example of an siRNA of the invention for targeting a corresponding mRNA sequence of SEQ ID NO: 2 and having 19-nucleotide strands and blunt ends is:

SEQ ID NO: 7
5'-UAGGCAAACUCCUUGACAA-3'

SEQ ID NO: 8
3'-AUCCGUUUGAGGAACUGUU-5'.

The strands of a double-stranded interfering RNA (e.g., an siRNA) may be connected to form a hairpin or stem-loop structure (e.g., an shRNA). An example of an shRNA of the invention targeting a corresponding mRNA sequence of SEQ ID NO:2 and having a 19 by double-stranded stem region and a 3'UU overhang is:

SEQ ID NO: 9

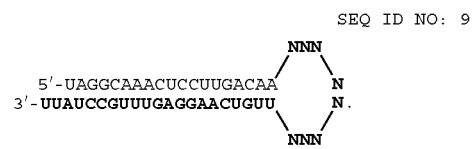

N is a nucleotide A, T, C, G, U, or a modified form known by one of ordinary skill in the art. The number of nucleotides N in the loop is a number between and including 3 to 23, or 5 to 15, or 7 to 13, or 4 to 9, or 9 to 11, or the number of nucleotides N is 9. Some of the nucleotides in the loop can be involved in base-pair interactions with other nucleotides in the loop. Examples of oligonucleotide sequences that can be used to form the loop include 5'-UUCAAGAGA-3' (Brummelkamp, T. R. et al. (2002) Science 296: 550) and 5'-UUUGUGUAG-3' (Castanotto, D. et al. (2002) RNA 8:1454). It will be recognized by one of skill in the art that the resulting single chain oligonucleotide forms a stem-loop or hairpin structure comprising a double-stranded region capable of interacting with the RNAi machinery.

The siRNA target sequence identified above can be extended at the 3'end to facilitate the design of dicer-substrate 27-mer duplexes. For example, extension of the 19-nucleotide DNA target sequence (SEQ ID NO: 2) identified in the Cx43 DNA sequence (SEQ ID NO: 1) by 6 nucleotides yields a 25-nucleotide DNA target sequence present at nucleotides 227 to 251 of SEQ ID NO: 1:

```
                                              SEQ ID NO: 10
    5'-UAGGCAAACUCCUUGACAAGGUUCA-3'.
```

An example of a dicer-substrate 27-mer duplex of the invention for targeting a corresponding mRNA sequence of SEQ ID NO: 10 is:

```
                                              SEQ ID NO: 11
    5'-UAGGCAAACUCCUUGACAAGGUUCA-3'

SEQ ID NO: 12
    3'-UUAUCCGUUUGAGGAACUGUUCCAAGU-5'.
```

The two nucleotides at the 3' end of the sense strand (i.e., the GU nucleotides of SEQ ID NO: 120) may be deoxynucleotides for enhanced processing. Design of dicer-substrate 27-mer duplexes from 19-21 nucleotide target sequences, such as provided herein, is further discussed by the Integrated DNA Technologies (IDT) website and by Kim D-H et al., (February, 2005) *Nature Biotechnology* 23:2; 222-226.

The target RNA cleavage reaction guided by siRNAs and other forms of interfering RNA is highly sequence specific. For example, in general, an siRNA molecule contains a sense nucleotide strand identical in sequence to a portion of the target mRNA and an antisense nucleotide strand exactly complementary to a portion of the target for inhibition of mRNA expression. However, 100% sequence complementarity between the antisense siRNA strand and the target mRNA, or between the antisense siRNA strand and the sense siRNA strand, is not required to practice the present invention, so long as the interfering RNA can recognize the target mRNA and silence expression of the Cx43 gene. Thus, for example, the invention allows for sequence variations between the antisense strand and the target mRNA and between the antisense strand and the sense strand, including nucleotide substitutions that do not affect activity of the interfering RNA molecule, as well as variations that might be expected due to genetic mutation, strain polymorphism, or evolutionary divergence, wherein the variations do not preclude recognition of the antisense strand to the target mRNA.

In one embodiment of the invention, interfering RNA of the invention has a sense strand and an antisense strand, and the sense and antisense strands comprise a region of at least near-perfect contiguous complementarity of at least 19 nucleotides. In another embodiment of the invention, an interfering RNA of the invention has a sense strand and an antisense strand, and the antisense strand comprises a region of at least near-perfect contiguous complementarity of at least 19 nucleotides to a target sequence of Cx43 mRNA, and the sense strand comprises a region of at least near-perfect contiguous identity of at least 19 nucleotides with a target sequence of Cx43 mRNA, respectively. In a further embodiment of the invention, the interfering RNA comprises a region of at least 13, 14, 15, 16, 17, or 18 contiguous nucleotides having percentages of sequence complementarity to or, having percentages of sequence identity with, the penultimate 13, 14, 15, 16, 17, or 18 nucleotides, respectively, of the 3' end of the corresponding target sequence within an mRNA. The length of each strand of the interfering RNA comprises about 19 to about 49 nucleotides, and may comprise a length of about 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49 nucleotides.

In certain embodiments, the antisense strand of an interfering RNA of the invention has at least near-perfect contiguous complementarity of at least 19 nucleotides with the target mRNA. "Near-perfect," as used herein, means the antisense strand of the siRNA is "substantially complementary to," and the sense strand of the siRNA is "substantially identical to" at least a portion of the target mRNA. "Identity," as known by one of ordinary skill in the art, is the degree of sequence relatedness between nucleotide sequences as determined by matching the order and identity of nucleotides between the sequences. In one embodiment, the antisense strand of an siRNA having 80% and between 80% up to 100% complementarity, for example, 85%, 90% or 95% complementarity, to the target mRNA sequence are considered near-perfect complementarity and may be used in the present invention. "Perfect" contiguous complementarity is standard Watson-Crick base pairing of adjacent base pairs. "At least near-perfect" contiguous complementarity includes "perfect" complementarity as used herein. Computer methods for determining identity or complementarity are designed to identify the greatest degree of matching of nucleotide sequences, for example, BLASTN (Altschul, S. F., et al. (1990) *J. Mol. Biol.* 215:403-410).

The term "percent identity" describes the percentage of contiguous nucleotides in a first nucleic acid molecule that is the same as in a set of contiguous nucleotides of the same length in a second nucleic acid molecule. The term "percent complementarity" describes the percentage of contiguous nucleotides in a first nucleic acid molecule that can base pair in the Watson-Crick sense with a set of contiguous nucleotides in a second nucleic acid molecule.

The relationship between a target mRNA and one strand of an siRNA (the sense strand) is that of identity. The sense strand of an siRNA is also called a passenger strand, if present. The relationship between a target mRNA and the other strand of an siRNA (the antisense strand) is that of complementarity. The antisense strand of an siRNA is also called a guide strand.

There may be a region or regions of the antisense siRNA strand that is (are) not complementary to a portion of SEQ ID NO: 1. Non-complementary regions may be at the 3', 5' or both ends of a complementary region or between two complementary regions. A region can be one or more bases.

The sense and antisense strands in an interfering RNA molecule can also comprise nucleotides that do not form base pairs with the other strand. For example, one or both strands can comprise additional nucleotides or nucleotides that do not pair with a nucleotide in that position on the other strand, such that a bulge or a mismatch is formed when the strands are hybridized. Thus, an interfering RNA molecule of the invention can comprise sense and antisense strands having mismatches, G-U wobbles, or bulges. Mismatches, G-U wobbles, and bulges can also occur between the antisense strand and its target (see, for example, Saxena et al., 2003, J Biol Chem.278:44312-9).

One or both of the strands of double-stranded interfering RNA may have a 3' overhang of from 1 to 6 nucleotides, which may be ribonucleotides or deoxyribonucleotides or a mixture thereof. The nucleotides of the overhang are not base-paired. In one embodiment of the invention, the interfering RNA comprises a 3' overhang of TT or UU. In another embodiment of the invention, the interfering RNA comprises at least one blunt end. The termini usually have a 5' phosphate group or a 3' hydroxyl group. In other embodiments, the antisense strand has a 5' phosphate group, and the sense strand has a 5' hydroxyl group. In still other embodiments, the termini are further modified by covalent addition of other molecules or functional groups.

The sense and antisense strands of the double-stranded siRNA may be in a duplex formation of two single strands as described above or may be a single-stranded molecule where the regions of complementarity are base-paired and are covalently linked by a linker molecule to form a hairpin loop when the regions are hybridized to each other. It is believed that the hairpin is cleaved intracellularly by a protein termed dicer to form an interfering RNA of two individual base-paired RNA molecules. A linker molecule can also be designed to comprise a restriction site that can be cleaved in vivo or in vitro by a particular nuclease.

In one embodiment, the invention provides an interfering RNA molecule that comprises a region of at least 13 contiguous nucleotides having at least 90% sequence complementarity to, or at least 90% sequence identity with, the penultimate 13 nucleotides of the 3' end of an mRNA corresponding to a DNA target, which allows a one nucleotide substitution within the region. Two nucleotide substitutions (i.e., 11/13=85% identity/complementarity) are not included in such a phrase. In another embodiment, the invention provides an interfering RNA molecule that comprises a region of at least 14 contiguous nucleotides having at least 85% sequence complementarity to, or at least 85% sequence identity with, the penultimate 14 nucleotides of the 3' end of an mRNA corresponding to a DNA target. Two nucleotide substitutions (i.e., 12/14=86% identity/complementarity) are included in such a phrase. In a further embodiment, the invention provides an interfering RNA molecule that comprises a region of at least 15, 16, 17, or 18 contiguous nucleotides having at least 80% sequence complementarity to, or at least 80% sequence identity with, the penultimate 14 nucleotides of the 3' end of an mRNA corresponding to a DNA target. Three nucleotide substitutions are included in such a phrase.

The penultimate base in a nucleic acid sequence that is written in a 5' to 3' direction is the next to the last base, i.e., the base next to the 3' base. The penultimate 13 bases of a nucleic acid sequence written in a 5' to 3' direction are the last 13 bases of a sequence next to the 3' base and not including the 3' base. Similarly, the penultimate 14, 15, 16, 17, or 18 bases of a nucleic acid sequence written in a 5' to 3' direction are the last 14, 15, 16, 17, or 18 bases of a sequence, respectively, next to the 3' base and not including the 3' base.

Interfering RNAs may be generated exogenously by chemical synthesis, by in vitro transcription, or by cleavage of longer double-stranded RNA with dicer or another appropriate nuclease with similar activity. Chemically synthesized interfering RNAs, produced from protected ribonucleoside phosphoramidites using a conventional DNA/RNA synthesizer, may be obtained from commercial suppliers such as Ambion Inc. (Austin, Tex. ), Invitrogen (Carlsbad, Calif.), or Dharmacon (Lafayette, Colo.). Interfering RNAs can be purified by extraction with a solvent or resin, precipitation, electrophoresis, chromatography, or a combination thereof, for example. Alternatively, interfering RNA may be used with little if any purification to avoid losses due to sample processing.

When interfering RNAs are produced by chemical synthesis, phosphorylation at the 5' position of the nucleotide at the 5' end of one or both strands (when present) can enhance siRNA efficacy and specificity of the bound RISC complex, but is not required since phosphorylation can occur intracellularly.

Interfering RNAs can also be expressed endogenously from plasmid or viral expression vectors or from minimal expression cassettes, for example, PCR generated fragments comprising one or more promoters and an appropriate template or templates for the interfering RNA. Examples of commercially available plasmid-based expression vectors for shRNA include members of the pSilencer series (Ambion, Austin, Tex.) and pCpG-siRNA (InvivoGen, San Diego, Calif.). Viral vectors for expression of interfering RNA may be derived from a variety of viruses including adenovirus, adeno-associated virus, lentivirus (e.g., HIV, FIV, and EIAV), and herpes virus. Examples of commercially available viral vectors for shRNA expression include pSilencer adeno (Ambion, Austin, Tex.) and pLenti6/ BLOCK-iT™-DEST (Invitrogen, Carlsbad, Calif.). Selection of viral vectors, methods for expressing the interfering RNA from the vector and methods of delivering the viral vector are within the ordinary skill of one in the art. Examples of kits for production of PCR-generated shRNA expression cassettes include Silencer Express (Ambion, Austin, Tex.) and siXpress (Mirus, Madison, Wis.).

In certain embodiments, a first interfering RNA may be administered via in vivo expression from a first expression vector capable of expressing the first interfering RNA and a second interfering RNA may be administered via in vivo expression from a second expression vector capable of expressing the second interfering RNA, or both interfering RNAs may be administered via in vivo expression from a single expression vector capable of expressing both interfering RNAs. Additional interfering RNAs can be administered in a like manner (i.e. via separate expression vectors or via a single expression vector capable of expressing multiple interfering RNAs).

Interfering RNAs may be expressed from a variety of eukaryotic promoters known to those of ordinary skill in the art, including pol III promoters, such as the U6 or H1 promoters, or pol II promoters, such as the cytomegalovirus promoter. Those of skill in the art will recognize that these promoters can also be adapted to allow inducible expression of the interfering RNA.

In certain embodiments of the present invention, an antisense strand of an interfering RNA hybridizes with an mRNA in vivo as part of the RISC complex.

"Hybridization" refers to a process in which single-stranded nucleic acids with complementary or near-complementary base sequences interact to form hydrogen-bonded complexes called hybrids. Hybridization reactions are sensitive and selective. In vitro, the specificity of hybridization (i.e., stringency) is controlled by the concentrations of salt or formamide in prehybridization and hybridization solutions, for example, and by the hybridization temperature; such procedures are well known in the art. In particular, stringency is increased by reducing the concentration of salt, increasing the concentration of formamide, or raising the hybridization temperature.

For example, high stringency conditions could occur at about 50% formamide at 37° C. to 42° C. Reduced stringency conditions could occur at about 35% to 25% formamide at 30° C. to 35° C. Examples of stringency conditions for hybridization are provided in Sambrook, J., 1989, Molecular Cloning: A Laboratory Manual, Cold Spring Harbor Laboratory Press, Cold Spring Harbor, N.Y. Further examples of stringent hybridization conditions include 400 mM NaCl, 40 mM PIPES pH 6.4, 1 mM EDTA, 50° C. or 70° C. for 12-16 hours followed by washing, or hybridization at 70° C. in 1×SSC or 50° C. in 1×SSC, 50% formamide followed by washing at 70° C. in 0.3×SSC, or hybridization at 70° C. in 4×SSC or 50° C. in 4×SSC, 50% formamide followed by washing at 67° C. in 1×SSC. The temperature for hybridization is about 5-10° C. less than the melting temperature (Tm) of the hybrid where Tm is determined for hybrids between 19 and 49 base pairs in length using the following calculation: Tm ° C.=81.5+16.6(log10[Na+])+ 0.41 (% G+C)−(600/N) where N is the number of bases in the hybrid, and [Na+] is the concentration of sodium ions in the hybridization buffer.

The above-described in vitro hybridization assay provides a method of predicting whether binding between a candidate siRNA and a target will have specificity. However, in the context of the RISC complex, specific cleavage of a target can also occur with an antisense strand that does not demonstrate high stringency for hybridization in vitro.

Interfering RNAs may differ from naturally-occurring RNA by the addition, deletion, substitution or modification of one or more nucleotides. Non-nucleotide material may be bound to the interfering RNA, either at the 5' end, the 3' end, or internally. Such modifications are commonly designed to increase the nuclease resistance of the interfering RNAs, to improve cellular uptake, to enhance cellular targeting, to assist in tracing the interfering RNA, to further improve stability, or to reduce the potential for activation of the interferon pathway. For example, interfering RNAs may comprise a purine nucleotide at the ends of overhangs. Conjugation of cholesterol to the 3' end of the sense strand of an siRNA molecule by means of a pyrrolidine linker, for example, also provides stability to an siRNA.

Further modifications include a 3' terminal biotin molecule, a peptide known to have cell-penetrating properties, a nanoparticle, a peptidomimetic, a fluorescent dye, or a dendrimer, for example.

Nucleotides may be modified on their base portion, on their sugar portion, or on the phosphate portion of the molecule and function in embodiments of the present invention. Modifications include substitutions with alkyl, alkoxy, amino, deaza, halo, hydroxyl, thiol groups, or a combination thereof, for example. Nucleotides may be substituted with analogs with greater stability such as replacing a ribonucleotide with a deoxyribonucleotide, or having sugar modifications such as 2' OH groups replaced by 2' amino groups, 2' 0-methyl groups, 2' methoxyethyl groups, or a 2'-O, 4'-C methylene bridge, for example. Examples of a purine or pyrimidine analog of nucleotides include a xanthine, a hypoxanthine, an azapurine, a methylthioadenine, 7-deazaadenosine and O- and N-modified nucleotides. The phosphate group of the nucleotide may be modified by substituting one or more of the oxygens of the phosphate group with nitrogen or with sulfur (phosphorothioates). Modifications are useful, for example, to enhance function, to improve stability or permeability, or to direct localization or targeting.

In certain embodiments, an interfering molecule of the invention comprises at least one of the modifications as described above.

In certain embodiments, the invention provides pharmaceutical compositions (also referred to herein as "compositions") comprising an interfering RNA molecule of the invention. Pharmaceutical compositions are formulations that comprise interfering RNAs, or salts thereof, of the invention up to 99% by weight mixed with a physiologically acceptable carrier medium, including those described infra, and such as water, buffer, saline, glycine, hyaluronic acid, mannitol, and the like.

Interfering RNAs of the present invention are administered as solutions, suspensions, or emulsions. The following are examples of pharmaceutical composition formulations that may be used in the methods of the invention.

| | Amount in weight % |
|---|---|
| Interfering RNA | up to 99; 0.1-99; 0.1-50; 0.5-10.0 |
| Hydroxypropylmethylcellulose | 0.5 |
| Sodium chloride | 0.8 |
| Benzalkonium Chloride | 0.01 |
| EDTA | 0.01 |
| NaOH/HCl | q.s. pH 7.4 |
| Purified water (RNase-free) | q.s. 100 ml |

| | Amount in weight % |
|---|---|
| Interfering RNA | up to 99; 0.1-99; 0.1-50; 0.5-10.0 |
| Phosphate Buffered Saline | 1.0 |
| Benzalkonium Chloride | 0.01 |
| Polysorbate 80 | 0.5 |
| Purified water (RNase-free) | q.s. to 100% |

| | Amount in weight % |
|---|---|
| Interfering RNA | up to 99; 0.1-99; 0.1-50; 0.5-10.0 |
| Monobasic sodium phosphate | 0.05 |
| Dibasic sodium phosphate (anhydrous) | 0.15 |
| Sodium chloride | 0.75 |
| Disodium EDTA | 0.05 |
| Cremophor EL | 0.1 |
| Benzalkonium chloride | 0.01 |
| HCl and/or NaOH | pH 7.3-7.4 |
| Purified water (RNase-free) | q.s. to 100% |

| | Amount in weight % |
|---|---|
| Interfering RNA | up to 99; 0.1-99; 0.1-50; 0.5-10.0 |
| Phosphate Buffered Saline | 1.0 |
| Hydroxypropyl-β-cyclodextrin | 4.0 |
| Purified water (RNase-free) | q.s. to 100% |

As used herein the term "effective amount" refers to the amount of interfering RNA or a pharmaceutical composition comprising an interfering RNA determined to produce a therapeutic response in a mammal. Such therapeutically effective amounts are readily ascertained by one of ordinary skill in the art and using methods as described herein.

Generally, an effective amount of the interfering RNAs of the invention results in an extracellular concentration at the surface of the target cell of from 100 pM to 1000 nM, or from 1 nM to 400 nM, or from 5 nM to about 100 nM, or about 10 nM. The dose required to achieve this local concentration will vary depending on a number of factors including the delivery method, the site of delivery, the number of cell layers between the delivery site and the target cell or tissue, whether delivery is local or systemic, etc. The concentration at the delivery site may be considerably higher than it is at the surface of the target cell or tissue. Topical compositions can be delivered to the surface of the target organ, such as the eye, one to four times per day, or on an extended delivery schedule such as daily, weekly, bi-weekly, monthly, or longer, according to the routine discretion of a skilled clinician. The pH of the formulation is about pH 4.0 to about pH 9.0, or about pH 4.5 to about pH 7.4.

An effective amount of a formulation may depend on factors such as the age, race, and sex of the subject, the rate of target gene transcript/protein turnover, the interfering RNA potency, and the interfering RNA stability, for example. In one embodiment, the interfering RNA is delivered topically to a target organ and reaches the Cx43 mRNA-containing tissue such as the ciliary body at a therapeutic dose thereby ameliorating Cx43-associated disease process.

Therapeutic treatment of patients with interfering RNAs directed against Cx43 mRNA is expected to be beneficial over small molecule treatments by increasing the duration of action, thereby allowing less frequent dosing and greater patient compliance, and by increasing target specificity, thereby reducing side effects.

An "acceptable carrier" as used herein refers to those carriers that cause at most, little to no ocular irritation, provide suitable preservation if needed, and deliver one or more interfering RNAs of the present invention in a homogenous dosage. An acceptable carrier for administration of interfering RNA of embodiments of the present invention include the cationic lipid-based transfection reagents TransIT®-TKO (Mirus Corporation, Madison, Wis.), LIPOFECTIN®, Lipofectamine, OLIGOFECTAMINE™ (Invitrogen, Carlsbad, Calif.), or DHARMAFECT™ (Dharmacon, Lafayette, Colo.); polycations such as polyethyleneimine; cationic peptides such as Tat, polyarginine, or Penetratin (Antp peptide); nanoparticles; or liposomes. Liposomes are formed from standard vesicle-forming lipids and a sterol, such as cholesterol, and may include a targeting molecule such as a monoclonal antibody having binding affinity for cell surface antigens, for example. Further, the liposomes may be PEGylated liposomes.

The interfering RNAs may be delivered in solution, in suspension, or in bioerodible or non-bioerodible delivery devices. The interfering RNAs can be delivered alone or as components of defined, covalent conjugates. The interfering RNAs can also be complexed with cationic lipids, cationic peptides, or cationic polymers; complexed with proteins, fusion proteins, or protein domains with nucleic acid binding properties (e.g., protamine); or encapsulated in nanoparticles or liposomes. Tissue- or cell-specific delivery can be accomplished by the inclusion of an appropriate targeting moiety such as an antibody or antibody fragment.

Interfering RNA may be delivered via aerosol, buccal, dermal, intradermal, inhaling, intramuscular, intranasal, intraocular, intrapulmonary, intravenous, intraperitoneal, nasal, ocular, oral, otic, parenteral, patch, subcutaneous, sublingual, topical, or transdermal administration, for example.

In certain embodiments, treatment of ocular disorders with interfering RNA molecules is accomplished by administration of an interfering RNA molecule directly to the eye. Local administration to the eye is advantageous for a number or reasons, including: the dose can be smaller than for systemic delivery, and there is less chance of the molecules silencing the gene target in tissues other than in the eye.

A number of studies have shown successful and effective in vivo delivery of interfering RNA molecules to the eye. For example, Kim et al. demonstrated that subconjunctival injection and systemic delivery of siRNAs targeting VEGF pathway genes inhibited angiogenesis in a mouse eye (Kim et al., 2004, *Am. J. Pathol.* 165:2177-2185). In addition, studies have shown that siRNA delivered to the vitreous cavity can diffuse throughout the eye, and is detectable up to five days after injection (Campochiaro, 2006, *Gene Therapy* 13.:559-562).

Interfering RNA may be delivered directly to the eye by ocular tissue injection such as periocular, conjunctival, subtenon, intracameral, intravitreal, intraocular, subretinal, subconjunctival, retrobulbar, or intracanalicular injections; by direct application to the eye using a catheter or other placement device such as a retinal pellet, intraocular insert, suppository or an implant comprising a porous, non-porous, or gelatinous material; by topical ocular drops or ointments; or by a slow release device in the cul-de-sac or implanted adjacent to the sclera (transscleral) or in the sclera (intrascleral) or within the eye.

Intracameral injection may be through the cornea into the anterior chamber to allow the agent to reach the trabecular meshwork. Intracanalicular injection may be into the venous collector channels draining Schlemm's canal or into Schlemm's canal.

For ophthalmic delivery, an interfering RNA may be combined with ophthalmologically acceptable preservatives, co-solvents, surfactants, viscosity enhancers, penetration enhancers, buffers, sodium chloride, or water to form an aqueous, sterile ophthalmic suspension or solution. Solution formulations may be prepared by dissolving the interfering RNA in a physiologically acceptable isotonic aqueous buffer. Further, the solution may include an acceptable surfactant to assist in dissolving the interfering RNA. Viscosity building agents, such as hydroxymethyl cellulose, hydroxyethyl cellulose, methylcellulose, polyvinylpyrrolidone, or the like may be added to the compositions of the present invention to improve the retention of the compound.

In order to prepare a sterile ophthalmic ointment formulation, the interfering RNA is combined with a preservative in an appropriate vehicle, such as mineral oil, liquid lanolin, or white petrolatum. Sterile ophthalmic gel formulations may be prepared by suspending the interfering RNA in a hydrophilic base prepared from the combination of, for example, CARBOPOL®-940 (BF Goodrich, Charlotte, N.C.), or the like, according to methods known in the art. VISCOAT® (Alcon Laboratories, Inc., Fort Worth, Tex.) may be used for intraocular injection, for example. Other compositions of the present invention may contain penetration enhancing agents such as cremephor and TWEEN® 80 (polyoxyethylene sorbitan monolaureate, Sigma Aldrich, St. Louis, Mo.), in the event the interfering RNA is less penetrating in the eye.

In certain embodiments, the invention also provides a kit that includes reagents for attenuating the expression of an mRNA as cited herein in a cell. The kit contains an siRNA or an shRNA expression vector. For siRNAs and non-viral shRNA expression vectors the kit also contains a transfection reagent or other suitable delivery vehicle. For viral shRNA expression vectors, the kit may contain the viral vector and/or the necessary components for viral vector production (e.g., a packaging cell line as well as a vector comprising the viral vector template and additional helper vectors for packaging). The kit may also contain positive and negative control siRNAs or shRNA expression vectors (e.g., a non-targeting control siRNA or an siRNA that targets an unrelated mRNA). The kit also may contain reagents for assessing knockdown of the intended target gene (e.g., primers and probes for quantitative PCR to detect the target mRNA and/or antibodies against the corresponding protein for western blots). Alternatively, the kit may comprise an siRNA sequence or an shRNA sequence and the instructions and materials necessary to generate the siRNA by in vitro transcription or to construct an shRNA expression vector.

A pharmaceutical combination in kit form is further provided that includes, in packaged combination, a carrier means adapted to receive a container means in close confinement therewith and a first container means including an interfering RNA composition and an acceptable carrier. Such kits can further include, if desired, one or more of various conventional pharmaceutical kit components, such as, for example, containers with one or more pharmaceutically acceptable carriers, additional containers, etc., as will be readily apparent to those skilled in the art. Printed instructions, either as inserts or as labels, indicating quantities of the components to be administered, guidelines for administration, and/or guidelines for mixing the components, can also be included in the kit.

Those of skill in the art, in light of the present disclosure, will appreciate that obvious modifications of the embodiments disclosed herein can be made without departing from the spirit and scope of the invention. All of the embodiments disclosed herein can be made and executed without undue experimentation in light of the present disclosure. The full scope of the invention is set out in the disclosure and equivalent embodiments thereof.

The specification should not be construed to unduly narrow the full scope of protection to which the present invention is entitled.

While a particular embodiment of the invention has been shown and described, numerous variations and alternate embodiments will occur to those skilled in the art. Accordingly, the invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes to the claims that come within the meaning and range of equivalency of the claims are to be embraced within their scope. Further, all published documents, patents, and applications mentioned herein are hereby incorporated by reference, as if presented in their entirety.

The following example, including the experiments conducted and results achieved are provided for illustrative purposes only and are not to be construed as limiting the invention.

EXAMPLE 1

Interfering RNA for Specifically Silencing Cx43 in CPA-47 Cells

Transfection of bovine CPA-47 cells (American Type Culture Collection, Manassas, Va.) was accomplished using standard in vitro concentrations (0.1-10 nM) of bovine Cx43 siRNAs (siCx43 #1-4) or siGENOME Non-targeting siRNA #1 (siControl) and DharmaFECT™ 1 transfection reagent (Dharmacon, Lafayette, Colo.). All siRNAs were dissolved in 1× siRNA buffer, an aqueous solution of 20 mM KCl, 6 mM HEPES (pH 7.5), 0.2 mM $MgCl_2$. Control samples included a buffer control in which the volume of siRNA was replaced with an equal volume of 1× siRNA buffer (-siRNA). siCx43 #1 targeted GAGCAAAACUGGGC-CAAUU (SEQ ID NO: 79) in bovine Cx43 mRNA (start position=932 in the bovine sequence); siCx43 #2 targeted the sequence CUGAGAACCUACAUCAUCA (SEQ ID NO: 80) in bovine Cx43 mRNA (start position=467 in the bovine sequence); siCx43 #3 targeted the sequence in bovine Cx43 mRNA that starts at position 30, and targets SEQ ID NO: 2 in Table 1 above; and siCx43 #4 targeted the sequence in bovine Cx43 mRNA that starts at position 283, and also targets SEQ ID NO: 18 in Table 1 above. The Cx43 siRNAs were double-stranded interfering RNAs having specificity for 19-nucleotide sequences contained within the bovine Cx43 mRNA sequence (derived from Genbank accession number NM_ 174068; SEQ ID NO: 81).

Cx43 protein expression was determined by western blot using an anti-Cx43 antibody (BD Biosciences, San Diego, Calif.). As shown in FIG. 1, transfection with the negative control siRNA caused essentially no change in Cx43 protein expression. All four of the siRNAs tested caused a dramatic reduction in Cx43 protein expression at the 10 and 1 nM siRNA concentrations. Of the four siRNAs tested, siCx43 #3 appeared to be the most potent, causing a greater level of knock-down at the 0.1 nM concentration than the other three siRNAs. Bovine Cx43 siRNAs siCx43 #3 and siCx43 #4 also have a perfect match to the human Cx43 sequence; whereas bovine Cx43 siRNAs siCx43 #1 and siCx43 #2 each have a single mismatch to the human Cx43 sequence. Therefore, both siCx43 #3 and siCx43 #4 should exhibit similar efficacy against human Cx43.

It should be understood that the foregoing disclosure emphasizes certain specific embodiments of the invention and that all modifications or alternatives equivalent thereto are within the spirit and scope of the invention as set forth in the appended claims.

We claim:

1. A composition comprising an interfering RNA and a pharmaceutically acceptable carrier wherein said interfering RNA comprises a double stranded RNA having a first strand 19-49 nucleotides in length and a second strand 19-49 nucleotides in length wherein the first strand comprises SEQ ID NO: 79 or SEQ ID NO: 80.

2. The composition of claim 1, wherein the first strand and the second strand are each 19-27 nucleotides in length.

3. The composition of claim 2, wherein the first strand and the second strand are each 19-25 nucleotides in length.

4. The composition of claim 3, wherein the first strand and the second strand are each 19-23 nucleotides in length.

5. The composition of claim 1, wherein the interfering RNA molecule has blunt ends.

6. The composition of claim 1, wherein at least one strand of the interfering RNA molecule comprises a 3' overhang.

7. The composition of claim 6, wherein the 3' overhang comprises about 1 to about 6 nucleotides.

8. The composition of claim 7, wherein the 3' overhang comprises 2 nucleotides.

9. The composition of claim 1, wherein the interfering RNA molecule comprises at least one modified nucleotide.

10. The composition of claim 9 wherein the modified nucleotide is a 2'-modified nucleotide.

11. The composition of claim 10 wherein the 2'-modified nucleotide is selected from the group consisting of: 2'-deoxy nucleotide, 2'-amino nucleotide, 2'-O-methyl nucleotide, 2'-methoxyethyl nucleotide.

12. The composition of claim 1 wherein the sense strand or the antisense strand contains a phosphorothioate linkage.

13. The composition of claim 1, wherein the interfering RNA molecule is a siRNA.

* * * * *